United States Patent
Takeda

(10) Patent No.: US 11,911,221 B2
(45) Date of Patent: Feb. 27, 2024

(54) ULTRASOUND DIAGNOSTIC APPARATUS, CONTROL METHOD OF ULTRASOUND DIAGNOSTIC APPARATUS, AND COMPUTER-READABLE RECORDING MEDIUM STORING CONTROL PROGRAM OF ULTRASOUND DIAGNOSTIC APPARATUS

(71) Applicant: Konica Minolta, Inc., Tokyo (JP)

(72) Inventor: Yoshihiro Takeda, Tokyo (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days.

(21) Appl. No.: 17/662,328

(22) Filed: May 6, 2022

(65) Prior Publication Data

US 2022/0361850 A1   Nov. 17, 2022

(30) Foreign Application Priority Data

May 17, 2021   (JP) .................................. 2021-083083

(51) Int. Cl.
*A61B 8/08* (2006.01)
*A61B 8/06* (2006.01)
*A61B 8/00* (2006.01)

(52) U.S. Cl.
CPC .............. *A61B 8/5223* (2013.01); *A61B 8/06* (2013.01); *A61B 8/54* (2013.01)

(58) Field of Classification Search
CPC ........... A61B 8/5223; A61B 8/06; A61B 8/54; A61B 8/5269; A61B 8/488; A61B 8/5207; G01S 15/8915; G01S 15/8988; G01S 15/8981
See application file for complete search history.

(56) References Cited

U.S. PATENT DOCUMENTS

2015/0320395 A1\* 11/2015 Sato .......................... A61B 8/06
                                                           600/455
2019/0125310 A1\* 5/2019 Takeda ................. A61B 8/5269

FOREIGN PATENT DOCUMENTS

JP        2014-158698 A      9/2014
JP        2020092936 A   *  6/2020

\* cited by examiner

*Primary Examiner* — Baisakhi Roy
*Assistant Examiner* — Kaitlyn E Sebastian
(74) *Attorney, Agent, or Firm* — LUCAS & MERCANTI, LLP

(57) ABSTRACT

An ultrasound diagnostic apparatus including a hardware processor that: calculates a plurality of eigenvectors by performing principal component analysis on a time-series reflection wave data group; calculates a principal frequency component of a time direction represented by the plurality of eigenvectors; determines a reduction rate of each of the plurality of eigenvectors on a basis of the principal frequency component of each of the plurality of eigenvectors and a clutter component reduction condition that defines a reference frequency for reduction of a clutter component; calculates a filter coefficient for reduction of the clutter component on a basis of the plurality of eigenvectors, and the reduction rate corresponding to each of the plurality of eigenvectors; and generates blood flow image data by applying the filter coefficient to the time-series reflection wave data group.

14 Claims, 18 Drawing Sheets

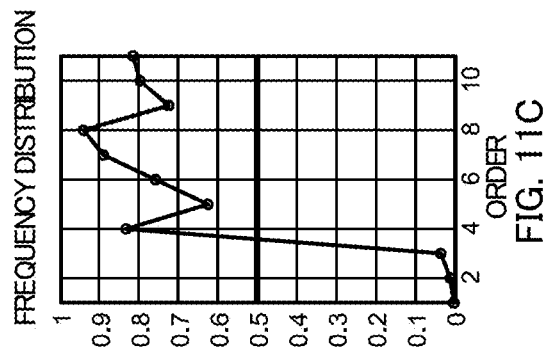
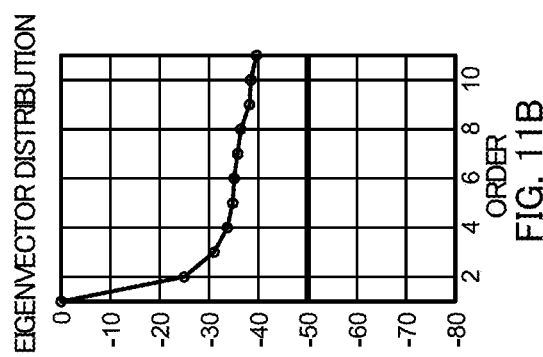
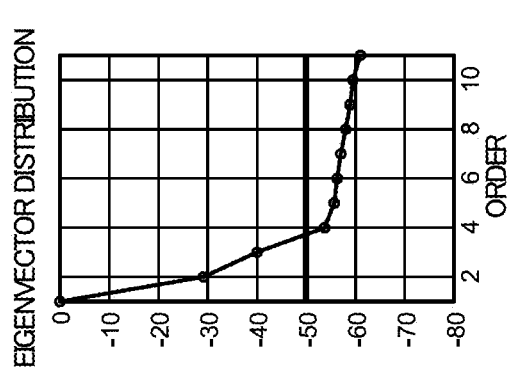
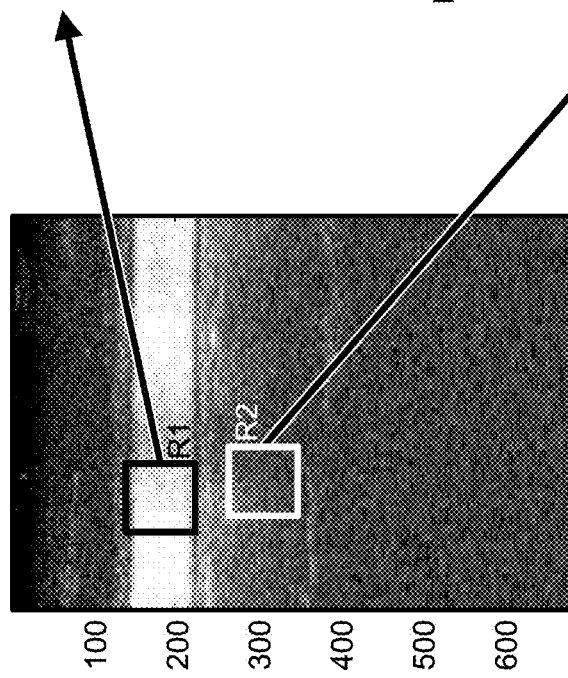
FIG. 11C
FIG. 11E
FIG. 11B
FIG. 11D
FIG. 11A

ULTRASOUND DIAGNOSTIC APPARATUS, CONTROL METHOD OF ULTRASOUND DIAGNOSTIC APPARATUS, AND COMPUTER-READABLE RECORDING MEDIUM STORING CONTROL PROGRAM OF ULTRASOUND DIAGNOSTIC APPARATUS

CROSS REFERENCE TO RELATED APPLICATIONS

The entire disclosure of Japanese Patent Application No. 2021-083083 filed on May 17, 2021 is incorporated herein by reference in its entirety.

BACKGROUND

Technological Field

The present disclosure relates to an ultrasound diagnostic apparatus, a control method of the ultrasound diagnostic apparatus, and a program for controlling the ultrasound diagnostic apparatus.

Description of Related Art

In ultrasound diagnosis, the heart beat and fetal movement can be obtained as ultrasound images by simply applying the ultrasound probe to the body surface, and the examination can be repeated because it is highly safe. Ultrasound diagnostic equipment is known to be used for ultrasound diagnosis and to generate and display ultrasound images. Also known is a diagnostic ultrasound device that generates and displays C (color flow (color Doppler) mode) images, which transmit and receive ultrasound waves to a specimen and display the flow of blood flow in the specimen in color using the Doppler method.

FIG. 22 illustrates the frequency characteristics of the power of a known moving target indication (MTI) filter. In the generation of C-mode image data, the frequency characteristics of the power of the Doppler signal corresponding to the received signal based on ultrasound reflected by the specimen are taken. Then, as illustrated in FIG. 22, the Doppler signal includes clutter component 201, blood flow component 202, and noise component 203. Clutter component 201 is the signal component of the tissue movement of the specimen. Blood flow component 202 is a signal component of the blood flow of the specimen. Noise component 203 is a signal component of system noise (random noise) specific to the device.

Generally, in order to image blood flow components in C-mode images, the clutter component 201 of the Doppler signal is removed by MTI filter 204. MTI filter 204 is a high-pass filter that removes the clutter component and extracts only the Doppler deviation component.

For example, an FIR filter using the difference in average velocity between the blood flow and clutter components is known as this MTI filter, as well as an applied MTI filter that varies its coefficients according to the input signal. The adaptive MTI filter obtains the velocity of the tissue from the signal before the MTI filter input and obtains a signal whose phase difference is canceled.

In particular, as an adaptive MTI filter of this type, an eigenvector MTI filter that performs principal component analysis using a correlation matrix from the Doppler signal before MTI filter input, discriminates between blood flow and clutter components based on principal components (eigenvectors) of each order, and thereby produces a blood flow image with clutter removed has attracted attention (see, for example, Japanese Patent Application Laid-Open No. 2014-158698). The eigenvector MTI filter is more useful than FIR filters in that it can remove the clutter component even when the frequency bands of the blood flow and clutter components overlap.

In known ultrasound systems that use this type of eigenvector MTI filter, a method is used to determine the appropriate rank cut order (eigenvector to be reduced) based on eigenvalues of eigenvectors of each order (i.e., principal components) obtained by principal component analysis to obtain blood flow images with clutter components removed.

FIG. 1 illustrates the processing of an eigenvector MTI filter for the known technology. FIG. 1 illustrates a blood flow image with only the eigenvector of the 0th order component reduced, a blood flow image with eigenvectors of the 0th to 1st order components reduced, a blood flow image with eigenvectors of the 0th to 2nd order components reduced . . . a blood flow image with eigenvectors of the 0th to nth order components (in FIG. 1, from 0 to 13th order components) reduced, in order from top left to bottom right.

The order of the multiple eigenvectors calculated by principal component analysis is set so that the order of the eigenvectors increases in descending order according to the magnitude of the eigenvalues. Since a clutter signal usually has higher signal strength (i.e., eigenvalues) than a blood flow signal, the order of the eigenvector is assigned such that the eigenvector with the lower order side is the eigenvector of the clutter signal and the eigenvector with the higher order side is the eigenvector of the blood flow component.

In the known technology, for example, the eigenvectors (i.e., principal components) of the order in which the magnitude of the eigenvalue of each eigenvector (i.e., principal component) is greater than a threshold are considered as clutter components and the rank cut order is determined (for example, FIG. 1 illustrates a situation in which the 4th order components are determined as rank cut order).

Such known technology is useful in that they can obtain blood flow images with clutter components removed by simple arithmetic processing. However, eigenvalues only represent the degree of information retained by the principal components, and the distribution of eigenvalues of each eigenvector of the zero-order to nth-order components is greatly affected by the strength of the blood flow signal in the region of interest (ROI) of the C-mode image and the strength of tissue movement. For example, the distribution of eigenvalues of each eigenvector of the zero-order to nth-order components is different in a region with a large amount of blood flow signals (e.g., carotid artery) and a region with a small amount of blood flow signals (e.g., thyroid gland) (see FIG. 11, below). Therefore, it is difficult to set an appropriate threshold for the eigenvalues to discriminate between the blood flow component and the clutter component.

In addition, although the clutter components are mostly concentrated in eigenvectors of higher eigenvalue orders, some of the clutter components are also included in eigenvectors of higher orders that represent blood flow components. Further, since the eigenvectors of higher orders that indicate blood flow components show little variation in eigenvalues between orders, it is difficult to determine the order of the boundary between eigenvectors of orders that contain many clutter components and eigenvectors of orders that contain many blood flow components.

Against this background, in ultrasound systems that use eigenvector MTI filters, the actual need arises for the user to seek the appropriate rank cut order while checking the ultrasound image.

SUMMARY

An object of the present disclosure is to provide an ultrasound diagnostic apparatus that can automatically set appropriate MTI filter characteristics, a control method of the ultrasound diagnostic apparatus, and a computer-readable recording medium storing the control program of the ultrasound diagnostic apparatus.

To solve the above-mentioned problems, an ultrasound diagnostic apparatus according to the present disclosure transmits ultrasound toward inside of a specimen and receives a reflection wave thereof to generate a blood flow image in the specimen, the ultrasound diagnostic apparatus comprising a hardware processor that: calculates a plurality of eigenvectors by performing principal component analysis on a time-series reflection wave data group in a predetermined region in the specimen obtained at execution of a color flow mode; calculates a principal frequency component of a time direction represented by the plurality of eigenvectors by performing frequency analyzation on each of the plurality of eigenvectors; determines a reduction rate of each of the plurality of eigenvectors on a basis of the principal frequency component of each of the plurality of eigenvectors and a clutter component reduction condition that defines a reference frequency for reduction of a clutter component; calculates a filter coefficient for reduction of the clutter component on a basis of the plurality of eigenvectors, and the reduction rate corresponding to each of the plurality of eigenvectors; and generates blood flow image data by applying the filter coefficient to the time-series reflection wave data group.

To solve the above-mentioned problems, a control method according to the present disclosure is a method of an ultrasound diagnostic apparatus that transmits ultrasound toward inside of a specimen and receives a reflection wave thereof to generate a blood flow image in the specimen, the control method comprising: a first process of calculating a plurality of eigenvectors by performing principal component analysis on a time-series reflection wave data group in a predetermined region in the specimen obtained at execution of a color flow mode; a second process of calculating a principal frequency component of a time direction represented by the plurality of eigenvectors by performing analyzation on each of the plurality of eigenvectors; a third process of determining a reduction rate of each of the plurality of eigenvectors on a basis of the principal frequency component of each of the plurality of eigenvectors and a clutter component reduction condition that defines a reference frequency for reduction of a clutter component; a fourth process of calculating a filter coefficient for reduction of the clutter component on a basis of the plurality of eigenvectors, and the reduction rate corresponding to each of the plurality of eigenvectors; and a fifth process of generating blood flow image data by applying the filter coefficient to the time-series reflection wave data group.

To solve the above-mentioned problems, a computer-readable recording medium according to the present disclosure is a medium storing a control program of an ultrasound diagnostic apparatus that transmits ultrasound toward inside of a specimen and receives a reflection wave thereof to generate a blood flow image in the specimen, the control program including: a first process of calculating a plurality of eigenvectors by performing principal component analysis on a time-series reflection wave data group in a predetermined region in the specimen obtained at execution of a color flow mode; a second process of calculating a principal frequency component of a time direction represented by the plurality of eigenvectors by performing analyzation on each of the plurality of eigenvectors; a third process of determining a reduction rate of each of the plurality of eigenvectors on a basis of the principal frequency component of each of the plurality of eigenvectors and a clutter component reduction condition that defines a reference frequency for reduction of a clutter component; a fourth process of calculating a filter coefficient for reduction of the clutter component on a basis of the plurality of eigenvectors, and the reduction rate corresponding to each of the plurality of eigenvectors; and a fifth process of generating blood flow image data by applying the filter coefficient to the time-series reflection wave data group.

BRIEF DESCRIPTION OF DRAWINGS

The advantages and features provided by one or more embodiments of the invention will become more fully understood from the detailed description given hereinbelow and the appended drawings which are given by way of illustration only, and thus are not intended as a definition of the limits of the embodiment of the present invention:

FIG. 11A, FIG. 11B, FIG. 11C, FIG. 11D and FIG. 11E are diagrams illustrating a distribution of an eigenvalue of an eigenvector of each order and a distribution of an eigenvector frequency that are obtained when principal component analysis is executed with a region of interest (for which a packet data group is to be acquired) set to a more local region;

DETAILED DESCRIPTION OF EMBODIMENTS

Figure 1:
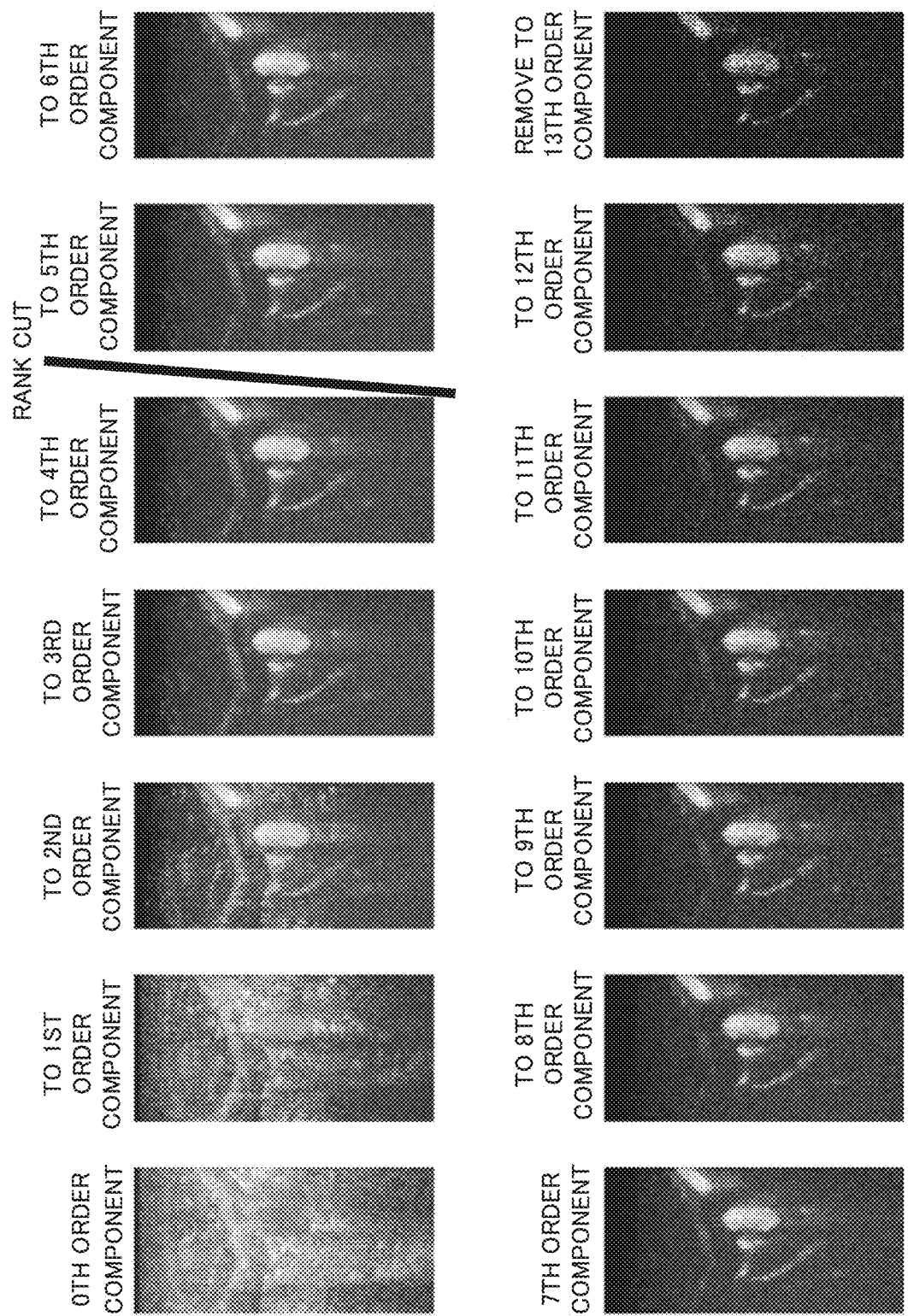
FIG. 1 is a diagram for describing a process of an eigenvector-type MTI filter according to known technology.

Hereinafter, one or more embodiments of the embodiment of the present invention will be described with reference to the drawings. However, the scope of the invention is not limited to the disclosed embodiments.

Preferred embodiments of the present disclosure will be elaborated below with reference to the drawings. Note that in the specification and drawings, the components with virtually identical function are denoted with the same reference numerals and overlapping description thereof will be omitted.

First Embodiment

First, a general configuration of ultrasound diagnostic apparatus 1 according to an embodiment is described below with reference to FIG. 2 to FIG. 4.

Figure 2:
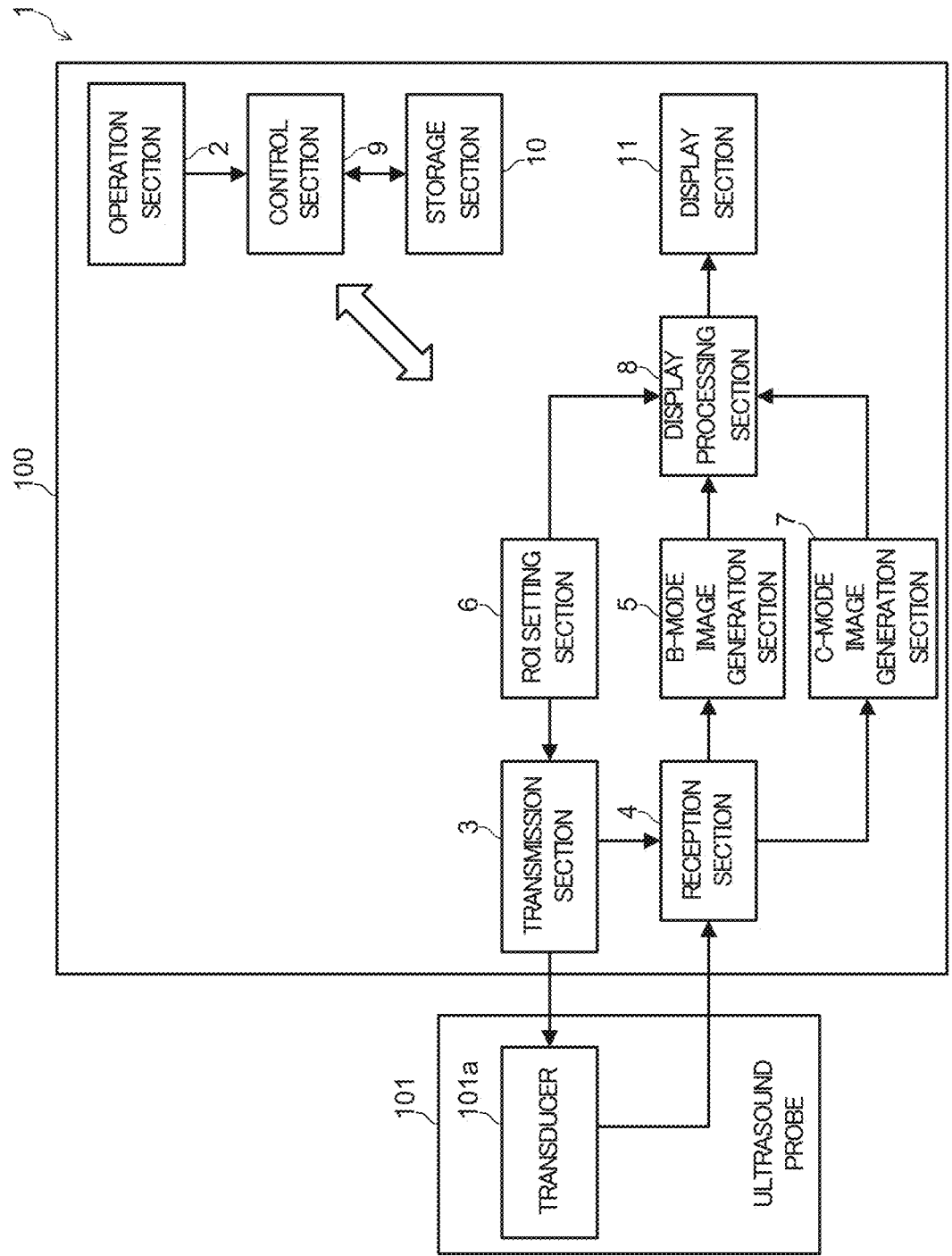
FIG. 2 is a schematic block diagram illustrating a configuration of an ultrasound diagnostic apparatus according to a first embodiment.

FIG. 2 is a schematic block diagram illustrating a configuration of ultrasound diagnostic apparatus 1 according to the present embodiment. FIG. 3 is a block diagram illustrating a functional configuration of C-mode image generation section 7 according to the present embodiment.

Ultrasound diagnostic apparatus 1 is an apparatus that is installed in medical facilities such as hospital, and generates an ultrasound image of a specimen such as patient's living body, which is a measurement object. Ultrasound diagnostic apparatus 1 is configured with ultrasound probe 101 connected to ultrasound diagnostic apparatus main body 100.

Ultrasound diagnostic apparatus main body 100 includes operation section 2, transmission section 3, reception section 4, brightness (B) mode image generation section 5, region of interest (ROI) setting section 6, C-mode image generation section 7, display processing section 8, control section 9, storage section 10, and display section 11.

Ultrasound probe 101 includes a plurality of transducers (piezoelectric conversion elements) 101a arranged in one dimensional direction, and each transducer 101a converts a driving signal (transmission electric signal) from transmission section 3 described later into ultrasound to generate an ultrasound beam. In this manner, the user applies the ultrasound beam to the inside of the specimen by placing ultrasound probe 101 at the surface of the specimen. Then, ultrasound probe 101 receives the ultrasound reflected from the inside of the specimen, converts the reflected ultrasound into a received electric signal at the plurality of transducers 101a, and supplies it to reception section 4 described later.

Note that while a linear ultrasound probe 101 in which the plurality of transducers 101a is arranged in one dimensional direction is described as an example in the present embodiment, this is not limitative. For example, it is also possible to use ultrasound probe 101 of a convex type, a sector type or the like in which the plurality of transducers 101a is arranged in one dimensional direction, ultrasound probe 101 in which the plurality of transducers 101a is two-dimensionally arranged, ultrasound probe 101 in which the plurality of transducers 101a arranged in one dimensional direction sways, and the like. In addition, under the control of control section 9, transmission section 3 can control the irradiation direction, the irradiation position and the like of the ultrasound beam transmitted by ultrasound probe 101 by selecting transducer 101a used by ultrasound probe 101 and individually changing the application timing and the value of the voltage applied to transducer 101a.

In addition, ultrasound probe 101 may have some functions of transmission section 3 and reception section 4 described later. For example, ultrasound probe 101 is configured to generate the driving signal in ultrasound probe 101 on the basis of a control signal for generating the driving signal (hereinafter referred to as "transmission control signal") output from transmission section 3, convert the driving signal into ultrasound by transducer 101a, convert the received reflected ultrasound into a received electric signal, and generate the received signal described later on the basis of the received electric signal in ultrasound probe 101.

Further, generally, ultrasound probe 101 is configured to be electrically connected to ultrasound diagnostic apparatus main body 100 through a cable, but this is not limitative. For example, ultrasound probe 101 may be configured to transmit and receive the transmission signal and the reception signal with ultrasound diagnostic apparatus main body 100, through wireless communication such as ultra wide band (UWB). It should be noted that with such a configuration, ultrasound diagnostic apparatus main body 100 and ultrasound probe 101 naturally include a communication section for wireless communication.

Operation section 2 receives an input from the user, and outputs a command based on the input of the user to control section 9. Operation section 2 allows the user to select a mode (hereinafter referred to as "B-mode") of displaying only the B-mode image indicating the amplitude of the reflected ultrasound as brightness (luminance), or a mode (hereinafter referred to as "C-mode") of displaying a C-mode (color flow mode) image on the B-mode image in a superimposed manner. Further, operation section 2 has a function of receiving a designation input of the user for the position of ROI to display the C-mode image on the B-mode image. In addition, the display mode of the C-mode image to be displayed further includes a V-mode for color display of the flow velocity and direction of the blood flow by blood flow velocity V as a blood flow signal representing the state of the blood flow, a P-mode for color display of the power of the blood flow by power P of the blood flow as the blood flow signal, and a V-T-mode for color display of the flow velocity and dispersion of the blood flow by dispersion T as blood flow velocity V and the blood flow signal. When an input of the C-mode is received from the user, operation section 2 further receives the input of the display mode. Note that the display mode of the C-mode image may include T (dispersion) mode, dP (directed power) mode and the like. In this manner, the C-mode includes a color Doppler mode (such as the V-mode and the V-T-mode), and a power Doppler mode (such as the P-mode).

In addition, operation section 2 may include a touch panel provided on the display screen of display section 11 and configured to receive a touch input of the user.

Transmission section 3 at least performs a transmission process of generating a driving signal and causing ultrasound probe 101 to transmit an ultrasound beam. As an example, transmission section 3 performs the transmission process of generating a driving signal for transmitting an ultrasound beam from ultrasound probe 101 including transducer 101a, and supplies to high pressure driving signal generated at a predetermined timing ultrasound probe 101 on the basis of the driving signal, to thereby drive transducer 101a of ultrasound probe 101. In this manner, ultrasound probe 101 can irradiate the specimen with the ultrasound beam by converting the driving signal to the ultrasound.

Under the control of control section 9, transmission section 3 performs the transmission process for displaying the C-mode image in addition to the transmission process for displaying the B-mode image in the case where the C-mode is on. For example, repetition of supply of a driving signal for displaying the C-mode image for n (e.g., n is dozens such as 16) times in the same direction (same line) after supply of an electrical driving signal for displaying the B-mode image is performed in all 360-degree directions (all lines) of the ROI set at ROI setting section 6. In addition, transmission section 3 designates the additional information of the transmission process for the B-mode image or for the transmission process for the C-mode image at the transmission process, and supplies the additional information to reception section 4.

Under the control of control section 9, reception section 4 performs a reception process of generating a received signal as electrical a high frequency (RF) signal based on the reflected ultrasound. For example, reception section 4 generates a received signal (sound ray data) by receiving the reflected ultrasound at ultrasound probe 101 and performing A/D conversion and phasing addition for the received electric signal converted based on the reflected ultrasound, by amplifying the received electric signal.

Reception section 4 acquires additional information from transmission section 3. Reception section 4 supplies the received signal to the B-mode image generation section 5 when the acquired additional information is additional information for the B-mode image, whereas it supplies the received signal to C-mode image generation section 7 when the acquired additional information is additional information for the C-mode image. In the following description, the received signal for the B-mode image generation is referred to as "B-mode received signal", and the received signal for the C-mode image generation is referred to as "C-mode received signal".

Note that in the present embodiment, reception section 4 sorts the received signal of the generated image frame into the signal for the B-mode image or the signal for the C-mode image, and supplies it to each block, but this is not limitative. For example, the received signal of the generated image frame may be sorted at each of B-mode image generation section 5 and C-mode image generation section 7.

Under the control of control section 9, B-mode image generation section 5 performs envelope detection, logarithmic compression and the like on the B-mode received signal input from reception section 4, performs luminance conversion through adjustment of the dynamic range and the gain so as to generate the B-mode image data and output it to display processing section 8.

Under the control of control section 9, ROI setting section 6 sets ROI (hereinafter also referred to as "region of interest") of the C-mode image to transmission section 3 and display processing section 8 in accordance with the designation information of the ROI input from the user through operation section 2.

Under the control of control section 9, C-mode image generation section 7 generates the C-mode image data in accordance with the C-mode received signal input from reception section 4, and outputs it to display processing section 8.

Figure 3:
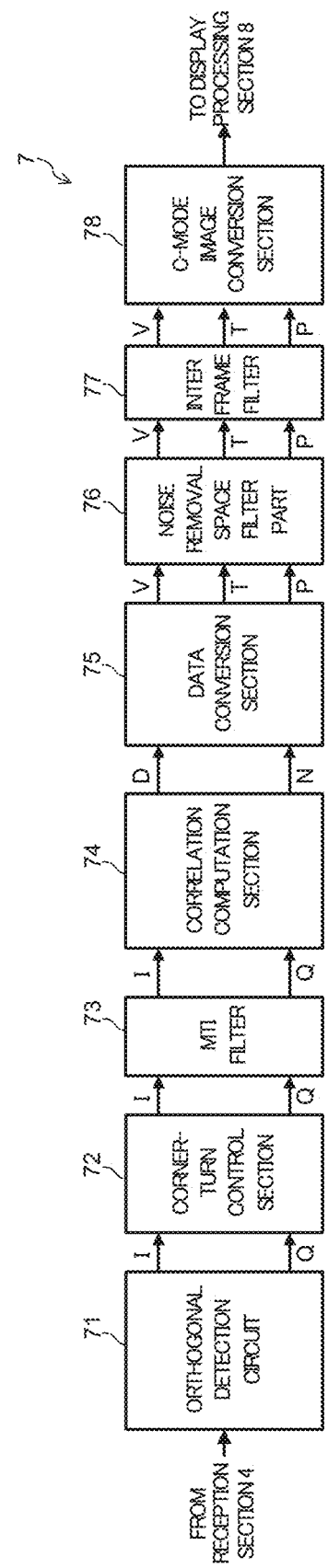
FIG. 3 is a block diagram illustrating a functional configuration of a C-mode image generation section according to the first embodiment.

C-mode image generation section 7 includes orthogonal detection circuit 71, corner-turn control section 72, MTI filter 73, correlation computation section 74, data conversion section 75, noise removal space filter part 76, inter frame filter 77, and C-mode image conversion section 78 (see FIG. 3). Note that correlation computation section 74, data conversion section 75, noise removal space filter part 76, inter frame filter 77, and C-mode image conversion section 78 function as "image generation section" of the embodiment of the present invention.

Under the control of control section 9, orthogonal detection circuit 71 performs orthogonal detection of the C-mode received signal input from reception section 4, calculates the phase difference between the acquired C-mode received signal and the reference signal, and acquires (complex) Doppler signal I,Q.

Under the control of control section 9, corner-turn control section 72 arranges the Doppler signal I,Q input from orthogonal detection circuit 71 in the depth direction from ultrasound probe 101 to the specimen and in the ensemble direction of the number of repetitions n of transmission and reception (hereinafter abbreviated as "repetitions") for each of the same acoustic lines (lines), stores the Doppler signal I,Q in a memory (not illustrated), and reads the Doppler signal I,Q in the ensemble direction at each depth.

In the received signal (Doppler signal I,Q), information (clutter component) of unnecessary vascular walls, tissues and the like are also mixed in addition to the blood flow signal component required for the C-mode image generation. Under the control of control section 9, MTI filter 73 removes the clutter component through the filtering of the Doppler signal I,Q input from corner-turn control section 72.

Next, an internal configuration of MTI filter 73 is described with reference to FIG. 4 to FIG. 11. Note that MTI filter 73 is the above-mentioned eigenvector-type MTI filter.

Figure 4:
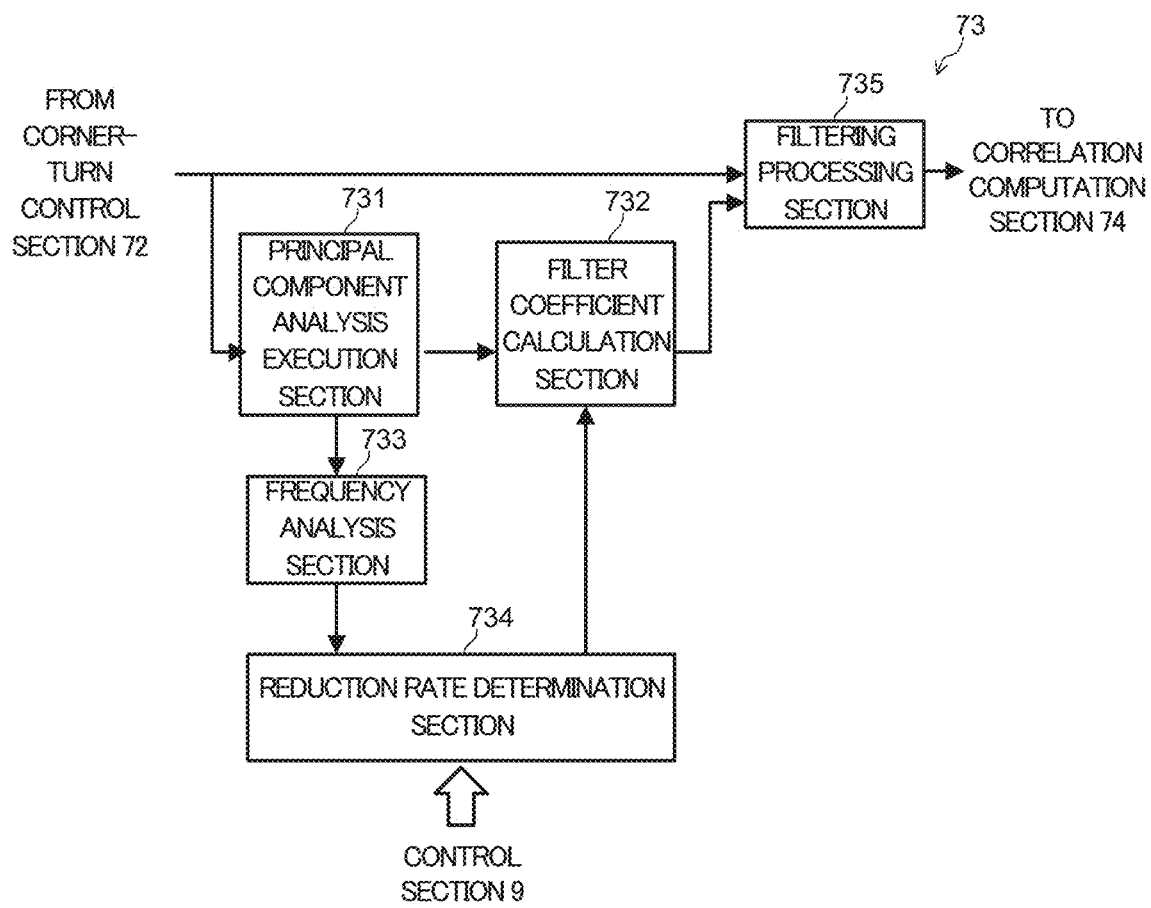
FIG. 4 is a diagram illustrating an internal configuration of an MTI filter according to the first embodiment.
Figure 5:
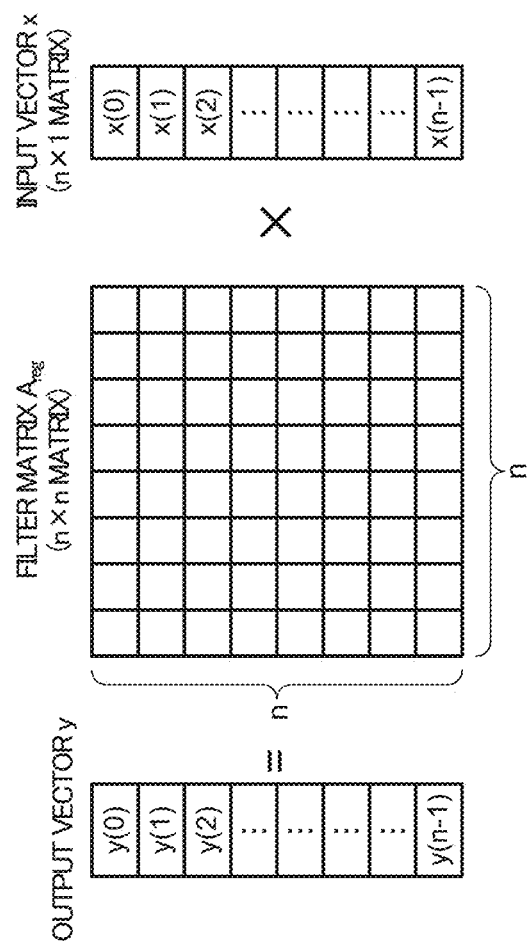
FIG. 5 is a diagram illustrating a relationship of input and output of the MTI filter.
Figure 6:
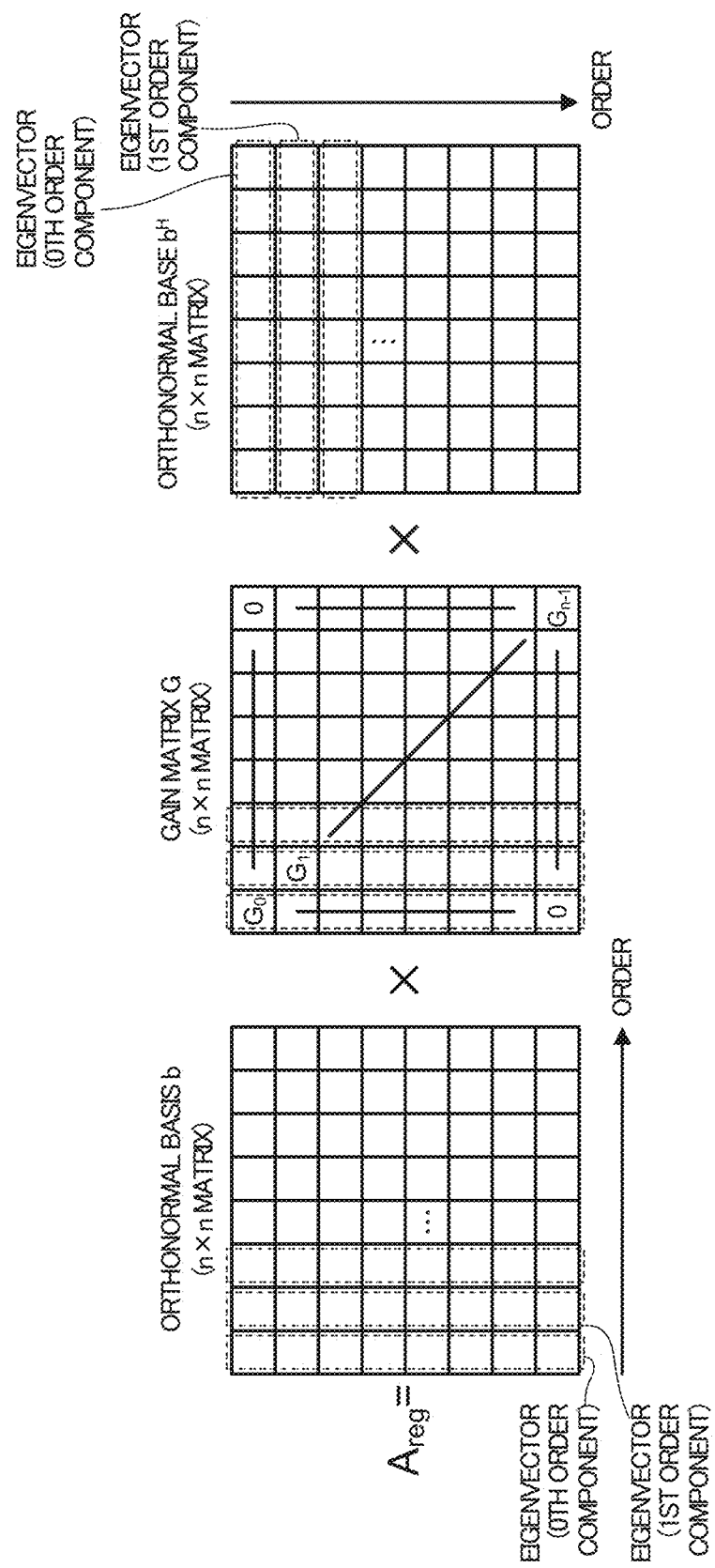
FIG. 6 is a diagram illustrating a method of calculation of an MTI filter coefficient of the MTI filter.
Figure 7:
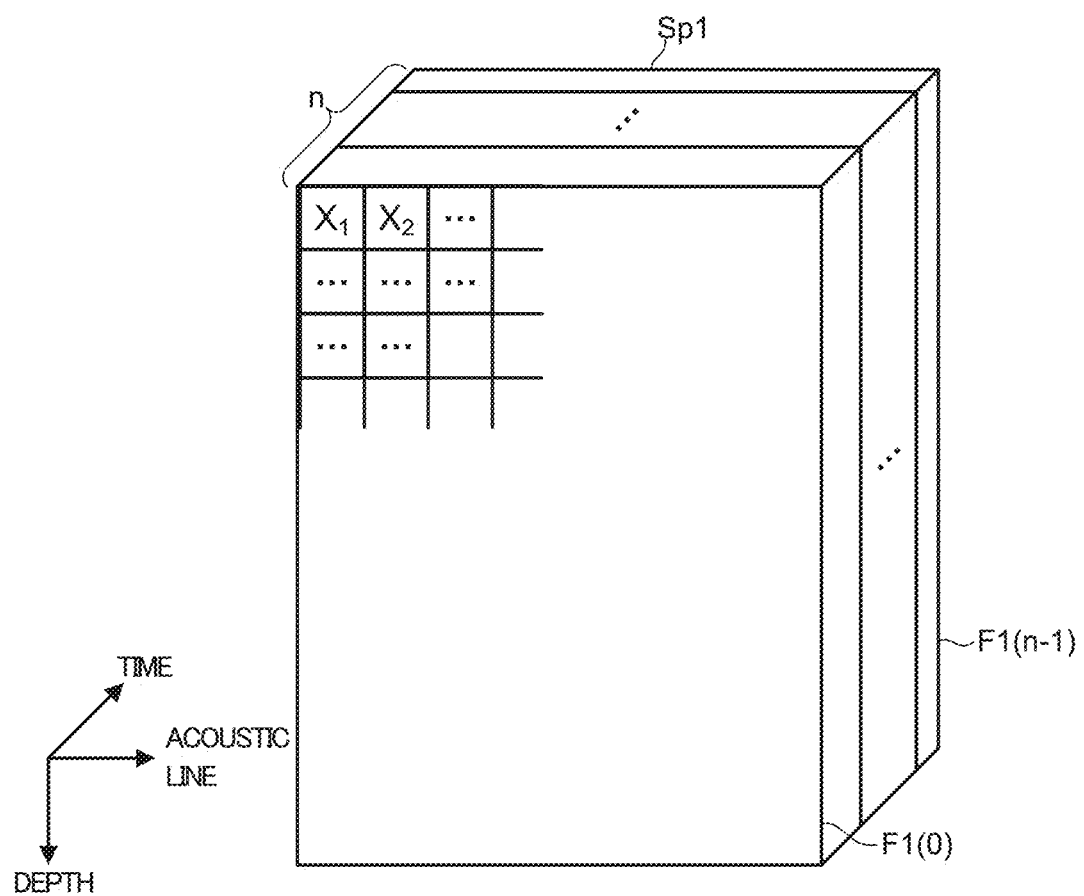
FIG. 7 is a diagram illustrating a data configuration of packet data used to obtain the C-mode image of one frame.

FIG. 4 is a diagram illustrating an internal configuration of MTI filter 73 according to the present embodiment. FIG. 5 is a diagram illustrating a relationship of input and output of MTI filter 73. FIG. 6 is a diagram illustrating a method of calculation of the MTI filter coefficient of MTI filter 73. FIG. 7 is a diagram illustrating a data configuration of packet data used for obtaining the C-mode image of one frame.

MTI filter 73 includes principal component analysis execution section 731, filter coefficient calculation section 732, frequency analysis section 733, reduction rate determination section 734, and filtering processing section 735.

In the color Doppler method, ultrasound scanning is performed within the region of interest while performing the transmission and reception of ultrasound in the same direction multiple times, and a blood flow signal is extracted from the time-series reflection wave data group received in this manner. The data sequence of the reflection wave signal (reflection wave data) from the same position obtained through the ultrasound transmission and reception is called packet. The packet size is the number of times of the ultrasound transmission and reception that are performed in the same direction to obtain the blood flow information of one frame. In a typical color Doppler method, the packet size is about 5 to 16.

The complex number of n repetitions (packet size n) composed of the Doppler signal I,Q output from corner-turn control section 72 is referred to as packet data Sp. In this case, the packet data Sp is represented by time-series n input data x (0), x (1), . . . , x (n−1) obtained from the same position. The x (0), x (1), . . . , x (n−1) are arranged in the time-series order in which they were generated or in reverse order.

The input and output of MTI filter 73 are represented by the following Expression (1), for example (see FIG. 5).

$$y = A_{reg} \times x \quad (1)$$

It should be noted that y: the output vector representing packet data y (0), y (1), . . . , y (n−1) output from the MTI filter, $A_{reg}$: the input vector representing MTI filter coefficient (n×n filter matrix), and x:input data x (0), x (1), . . . , x (n−1).

MTI filter 73 is represented by MTI filter coefficient $A_{reg}$ (filter matrix of n×n matrix) as expressed by the following Expression (2), for example (see FIG. 6).

$$A_{reg} = b \times G \times b^H \quad (2)$$

It should be noted that b: orthonormal basis (n×n matrix), G: gain matrix (n×n matrix), and $b^H$: orthonormal basis of b and Hermitian transpose (n×n matrix).

Orthonormal bases b, $b^H$ for calculating MTI filter 73 are composed of a plurality of eigenvectors obtained through a principal component analysis. Orthonormal bases b, $b^H$ are expressed such that the eigenvalues with the largest eigenvector are of 0th order, and the order increases in descending order according to the eigenvalue. That is, in orthonormal basis b, the larger the column number, the larger the order. In orthonormal basis $b^H$, the order also increases as the row number increases.

Diagonal components $G_0, G_1, \ldots, G_{n-1}$ of gain matrix G correspond to the clutter reduction rate of MTI filter 73. When the diagonal component is 0, the reduction rate corresponds to 100%, and when the diagonal component is 1, the reduction rate corresponds to 0%. Diagonal components $G_0, G_1, \ldots, G_{n-1}$ are the eigenvalues in ascending order according to the order. Diagonal components $G_0, G_1, \ldots, G_{n-1}$ are, for example, divided into values 0 and 1 at the boundary order corresponding to the rank cut order. The greater the clutter reduction rate of MTI filter 73, the more zeros there are in diagonal components $G_0, G_1, \ldots, G_{n-1}$. It should be noted that diagonal components $G_0, G_1, \ldots, G_{n-1}$ may be configured to take values other than 0 and 1, including decimal points between 0 and 1.

Note that in the present embodiment, orthonormal bases b, $b^H$ are determined by principal component analysis execution section 731, and the gain matrix G (diagonal components $G_0, G_1, \ldots, G_{n-1}$) is set by reduction rate determination section 734.

Principal component analysis execution section 731, filter coefficient calculation section 732, frequency analysis section 733, reduction rate determination section 734, and filtering processing section 735 are functional parts that execute the above-mentioned arithmetic processing, for example.

Principal component analysis execution section 731 calculates a plurality of eigenvectors making up the orthonormal bases b, $b^H$ by performing principal component analysis on the time-series reflection wave data group in the region of interest obtained at execution of the color flow mode.

To be more specific, first, principal component analysis execution section 731 acquires data of the packet data (hereinafter referred to as "packet data group Sp1") of each observation point in the region of interest set to ROI setting section 6 from corner-turn control section 72, and generates matrix C according to packet data group Sp1 (see Expression (3)) and matrix $C^H$ of Hermitian transpose of matrix C. Packet data group Sp1 includes input data x0, x1, . . . , xM according to each observation point in the region of interest corresponding to the packet size (i.e., corresponds to n repetitions), and matrix C is a matrix of n×M (see FIG. 7). Note that in packet data group Sp1, the packet data of each kth observation point in n repetitions is summarized in a frame unit, as F1(k−1).

[Math 1]

$$C = \frac{1}{\sqrt{M}} \begin{bmatrix} x_1(0) & \ldots & x_M(0) \\ \vdots & \ddots & \vdots \\ x_1(n-1) & \ldots & x_M(n-1) \end{bmatrix} \quad (3)$$

(It should be noted that M: the number of observation points in the region of interest, n: packet size, and the numbers in parentheses in input data x: the number of repetitions)

Next, from matrices C, $C^H$, principal component analysis execution section 731 calculates covariance matrix R using Expression (4).

$$R = C \times C^H \quad (4)$$

Then, principal component analysis execution section 731 calculates the eigenvalue and eigenvector (i.e., orthonormal bases b, $b^H$) by solving the eigenvalue problem (i.e., Rb=λb) for the covariance matrix R. At this time, principal component analysis execution section 731 calculates the eigenvalue and eigenvector for n orders corresponding to the packet size, for example. Then, principal component analysis execution section 731 sends the calculated eigenvalue and eigenvector to frequency analysis section 733, and MTI filter coefficient calculation section 732.

Note that for the calculated plurality of eigenvectors, principal component analysis execution section 731 sets the order of the eigenvector such that the eigenvalues with the largest eigenvector are of 0th order and the order increases in descending order according to the eigenvalue. Since a clutter signal usually has a greater signal strength (i.e., eigenvalue) than a blood flow signal, the order is assigned to the eigenvector such that the eigenvector on the lower order side is the eigenvector of the clutter signal and the eigenvector on the higher order side is the eigenvector of the blood flow component.

Frequency analysis section 733 calculates the principal frequency component of the time direction represented by the eigenvector for each of the eigenvectors of n orders calculated by principal component analysis execution section 731.

As described above, the inventors of the present application problematized the known technology that determines the rank cut order based on the eigenvalue of the eigenvector of each order, and a different approach from known technology was sought to determine the rate of reduction of eigenvectors for each order. Then, as a result of extensive study, a method has been achieved in which the principal frequency component of the time direction represented by each of a plurality of eigenvectors is calculated through frequency analyzation of each of a plurality of eigenvectors, and the reduction rate of the eigenvector is determined based on the principal frequency component of the time direction represented by the eigenvector.

The eigenvector is a space-time vector when expressed on the unique space obtained through the principal component analysis (i.e., a composite vector of a plurality of frequency vectors), and therefore cannot be compared with the frequency band of the clutter component as it is. In view of this, present inventors of the present application calculated the principal frequency component of the time direction represented by the eigenvector of each order through frequency analyzation of the eigenvector of each order by mathematical methods using the following Expression (5) and Expression (6). Note that the principal frequency component of the time direction represented by the eigenvector (hereinafter abbreviated as "principal frequency component represented by eigenvector" or "eigenvector frequency") means an average frequency of time variation of the observation object position represented by the eigenvector, for example.

Expression (5) is an expression for calculating the autocorrelation value (in this case, an autocorrelation value of lag difference of 1 in n number of iterations) of the eigenvector of each order of the reflection wave signal from the same position. The autocorrelation value is a measure of matching of a signal with its own time-shifted signal. Here, with Expression (5), the phase difference component of the time direction represented by the eigenvector of each order (i.e., phase variation velocity) can be calculated. Then, with Expression (6), the phase difference component of the time direction represented by the eigenvector of each order is converted into a frequency component of the time direction (eigenvector frequency).

[Math 2]

$$AC(1)_k = \sum_{m=0}^{n-2} w_m \times e_k(m+1) \times e_k^*(m) \quad (5)$$

(note that $e_k$: eigenvector of kth order, $e_k(m)$: an element of mth column of eigenvector $e_k$, and a complex Doppler signal of mth ultrasound of n repetitions expressed in unique space, and $w_m$: a weight to a value of mth column of eigenvector $e_k$)

[Math 3]

$$f_k = \frac{\arg\{AC(1)_k\}}{\pi} \quad (6)$$

(note that $f_k$ is a value of −1 to +1)

In this manner, frequency analysis section 733 achieves comparison with the frequency band of the clutter component by calculating the principal frequency component of the time direction represented by the eigenvector of each order.

Note that in Expression (5), weight $w_m$ for the value of mth column of eigenvector $e_k$ is a coefficient for weight average of each complex Doppler signal of ultrasound of n repetitions. The weight $w_m$ is set such that the complex Doppler signal of the first and nth ultrasounds of n repetitions are small, for example. In this manner, it is possible to reduce the proportion of the first and nth complex Doppler signals that correspond to the switching timing of the transmission and reception position of the ultrasound and tend to be unstable complex Doppler signals. It should be noted that any weight $w_m$ may be set.

Reduction rate determination section 734 determines the reduction rate of the eigenvector of each order on the basis of the principal frequency component (eigenvector frequency) represented by the eigenvector of each order, and a clutter component reduction condition that defines the reference frequency for reduction of the clutter component. Then, reduction rate determination section 734 sets gain matrix G of Expression (2) from the determined reduction rate of the eigenvector of each order, and outputs it to MTI filter coefficient calculation section 732.

The reference frequency is a frequency of time variation serving as a reference for identifying the frequency component of the blood flow signal and the frequency component of the clutter signal, and is typically set to an intermediate frequency of a typical frequency of a blood flow signal and a typical frequency of a clutter signal. The clutter component reduction condition is stored in storage section 10 in advance, for example. Note that here, the reference frequency is a fixed value, but it is preferable that the reference frequency be adjustable by the user operation. In addition, it is preferable that the reference frequency be automatically adjusted on the basis of the transmission/reception condition of the ultrasound at the execution of the color flow mode (as described later in second to sixth embodiments).

For example, reduction rate determination section 734 compares the eigenvector frequency and the reference frequency for the eigenvector of each order, and reduction rate determination section 734 determines the reduction rate of the eigenvector to be 0 when the eigenvector frequency is generates the reference frequency, whereas reduction rate determination section 734 determines the reduction rate of the eigenvector to be 1 when the eigenvector frequency is smaller than the reference frequency. Note that here, the reference frequency is a threshold at the determination of the rank cut order (hereinafter referred to as "threshold").

Figure 8:
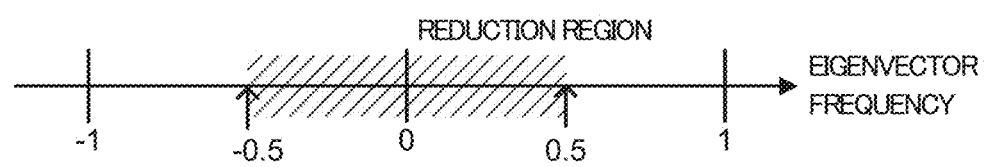
FIG. 8 is a diagram illustrating a process of a reduction rate determination section according to the first embodiment.

FIG. 8 is a diagram illustrating an example of a process of reduction rate determination section 734 according to the present embodiment. FIG. 8 illustrates a method of determining the rank cut order with respect to the eigenvector frequency by reduction rate determination section 734. Note that in the clutter component reduction condition according to the present embodiment, "0.5" (denoted as an absolute value; the same shall apply hereinafter) is set as a value of the reference frequency. The reduction rate is set to 0 for an eigenvector whose eigenvector frequency is greater than "0.5", and the reduction rate of an eigenvector whose eigenvector frequency is smaller than "0.5" is set to 1. Here, the eigenvector frequency is calculated as a value of −1 to +1 by Expression (6).

Now, a difference between a rank cut order determination method of known technology and the rank cut order determination method according to the embodiment of the present invention is described with reference to FIG. 9A, FIG. 9B, FIG. 10A, FIG. 10B, and FIG. 11.

Figure 9A:
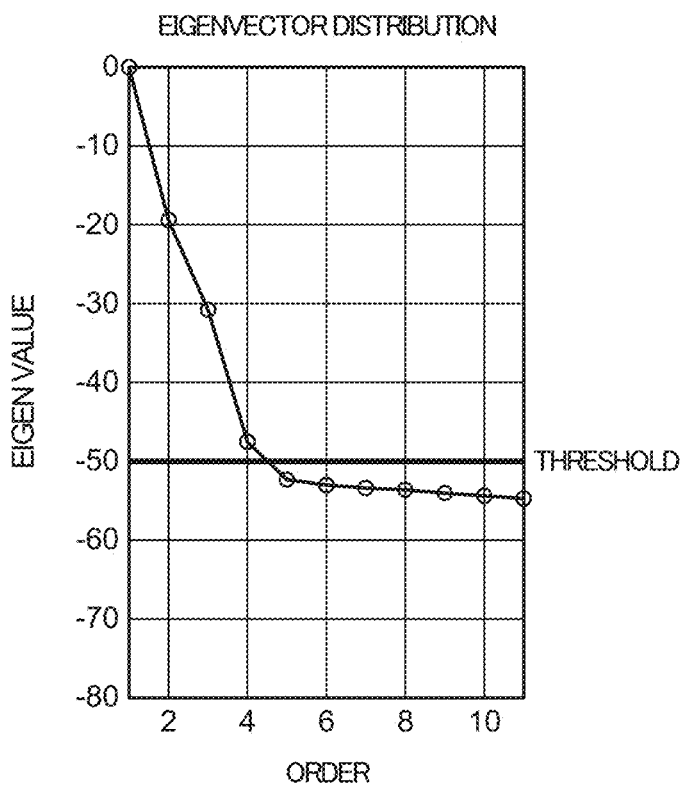
FIG. 9A is a diagram illustrating a rank cut order determination method according to known technology.
Figure 9B:
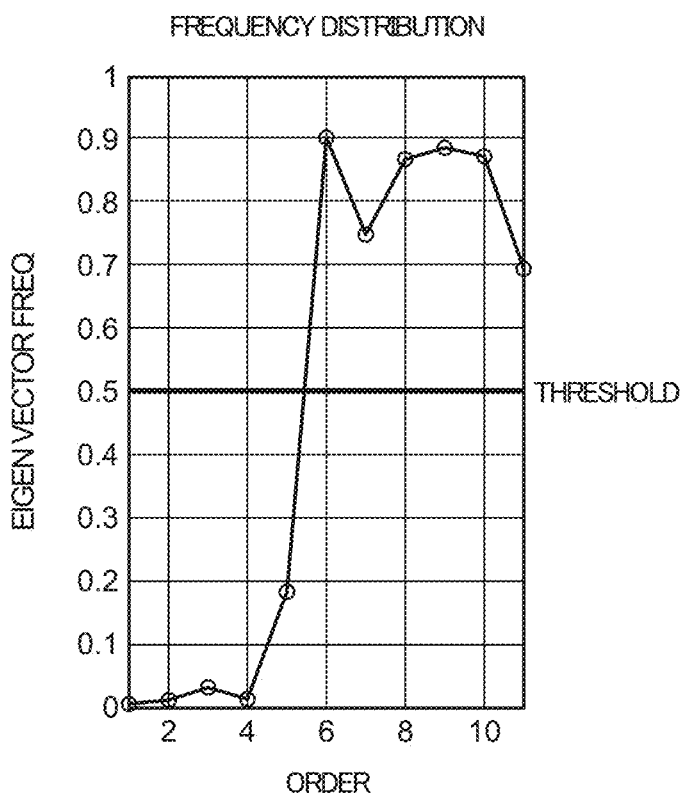
FIG. 9B is a diagram illustrating a rank cut order determination method according to an embodiment of the present invention.

FIG. 9A is a diagram illustrating a rank cut order determination method of known technology. FIG. 9B is a diagram illustrating the rank cut order determination method according to the embodiment of the present invention. FIG. 9A and FIG. 9B illustrate data of the eigenvectors for the same n (in this case, 12) orders calculated by principal component analysis execution section 731. Note that the ordinate in FIG. 9A indicates the eigenvector of each order eigenvalue, and the ordinate in FIG. 9B indicates the eigenvector of each order eigenvector frequency.

Figure 10A:
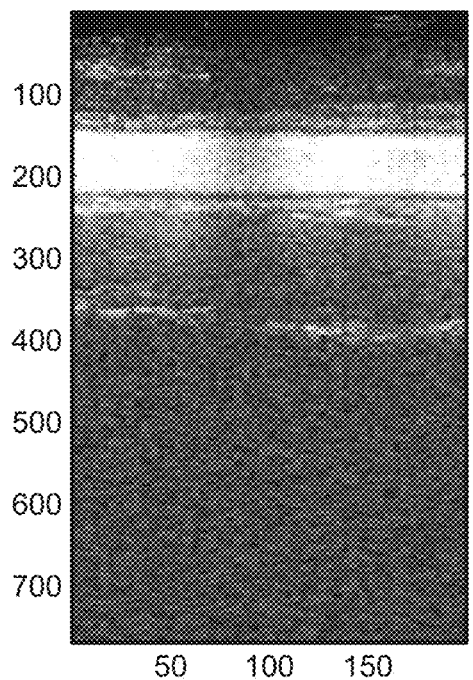
FIG. 10A is a blood flow image that is generated when the rank cut order is determined by the determination method of the rank cut order according to known technology (FIG. 9A)
Figure 10B:
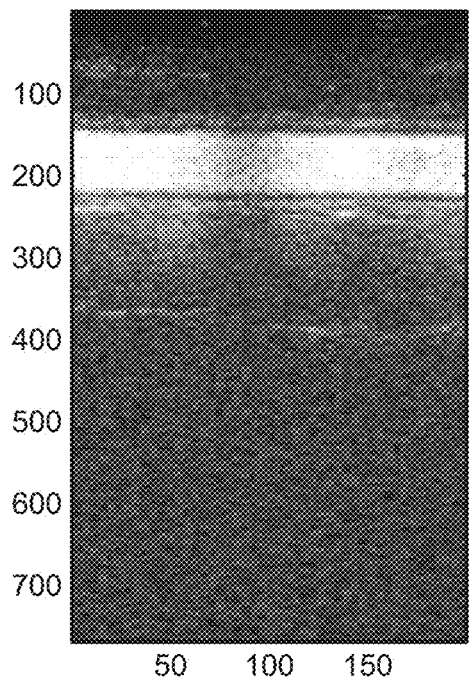
FIG. 10B is a blood flow image that is generated when a rank cut order is determined by the rank cut order determination method according to the embodiment of the present invention (FIG. 9B)

FIG. 10A shows a blood flow image that is generated when the rank cut order is determined by a rank cut order determination method of known technology (FIG. 9A), and FIG. 10B shows a blood flow image that is generated when the rank cut order is determined by the rank cut order determination method according to the embodiment of the present invention (FIG. 9B).

FIG. 9A illustrates a mode in which the rank cut order is determined with a threshold "eigenvalue: −50". In the rank cut order determination method of known technology in FIG. 9A, the reduction rate of the order eigenvector whose eigenvalue is greater than −50 is determined to be 1, and the reduction rate of the order eigenvector whose eigenvalue is −50 or smaller is determined to be 0. In this manner, in FIG. 9A, the eigenvectors of the zeroth order to fourth order are removed from the packet data group after the MTI filter process (i.e., blood flow image).

FIG. 9B illustrates a mode in which the rank cut order is determined with "eigenvector frequency: 0.5" as the threshold (in this case, this means the reference frequency). In the rank cut order determination method according to the embodiment of the present invention in FIG. 9B, the reduction rate of the eigenvector of the order whose eigenvector frequency is smaller than 0.5 is determined to be 1, and the reduction rate of the eigenvector whose eigenvector frequency of the order is 0.5 or greater is determined to be 0. In this manner, in FIG. 9B, the eigenvectors of the zeroth order to fifth order are removed from the packet data group after the MTI filter process (i.e., blood flow image).

A difference between a case that employs the rank cut order determination method of known technology, and a case that embodiment the rank cut order determination method according to the embodiment of the present invention in the modes of FIG. 9A and FIG. 9B is whether the eigenvector of the fifth order is regarded as a reflection wave component that is dependent on the clutter signal. It should be noted that as can be seen from FIG. 9B, in practice, the eigenvector frequency of the fifth order represents a low frequency component, and it is highly possible that it represents the clutter signal. Consequently, in the case where the rank cut order determination method of known technology is employed, a blood flow image in which the clutter signal dependent on the eigenvector frequency of the fifth order remains (FIG. 10A) may be generated, and the clearness of the image quality representing the blood flow signal is inferior to the blood flow image (FIG. 10B) that is generated in the case where the rank cut order is determined by the rank cut order determination method according to the embodiment of the present invention (FIG. 9B).

FIG. 11 is a diagram illustrating the distribution of the eigenvalue of the eigenvector of each order and the distribution of the eigenvector frequency that are obtained when the principal component analysis is executed with the region of interest (packet data group acquisition of object) set to a more local region. FIG. 11B and FIG. 11C are diagrams illustrating the distribution of the eigenvalue of the eigenvector of each order (FIG. 11B), and the distribution of the eigenvector frequency (FIG. 11C) that are obtained by the principal component analysis in the case where the region of interest is set to a region of a thick blood vessel (region R1 of FIG. 11A), and FIG. 11D and FIG. 11E are diagrams illustrating the distribution of the eigenvalue of the eigenvector of each order (FIG. 11D), and the distribution of the eigenvector frequency (FIG. 11E) that are obtained by the principal component analysis in the case where the region of interest is set to a region of a thin blood vessel (region R2 of FIG. 11A).

FIG. 11A to FIG. 11E show that the eigenvalue is largely changed by the signal strength of the blood flow signal and the clutter signal in the region of the observation object (see FIG. 11B and FIG. 11D). Therefore, in this example, when setting the threshold for determining the rank cut order in accordance with the distribution of the eigenvalue of FIG. 11B, the clutter signal is floated in the distribution of the eigenvalue of FIG. 11D.

On the other hand each of the eigenvector frequency of the clutter signal and the eigenvector frequency of the blood flow signal appears in substantially the same frequency band without depending on the signal strength of the clutter signal and the blood flow signal in the region of the observation object (see FIG. 11C and FIG. 11E).

In this manner, the distribution of the eigenvalue of each of the eigenvectors of the 0th order component to the nth order component largely depends on the strength of the blood flow signal at the region of interest of the imaging object of the C-mode image, and the strength of the tissue movement, and the distribution of the eigenvalue differs between the region where a large number of blood flow signals is present (e.g., carotid artery) and the region where a small number of blood flow signals is present (e.g., thyroid gland). Further, the high order eigenvector representing the blood flow signal has small variation of the eigenvalue between the orders, and it is difficult to determine the boundary order of the eigenvector of the order having a large number of clutter components and the eigenvector of the order having a large number of blood flow signals.

In view of this, if whether to reduce the eigenvector is determined based on the threshold of the eigenvalue of the eigenvector, a large number of clutter signals may remain, or the blood flow signal may also be removed.

In view of this, in the present invention, the reduction rate of the eigenvector of each order is determined by performing the frequency analyzation of the eigenvector of each order, calculating the principal frequency component represented by the eigenvector of each order, and comparing the principal frequency component by represented by the eigenvector of each order with the frequency component of the actual clutter signal. In this manner, the reduction rate of the eigenvector of each order can be appropriately determined.

At this time, in the principal frequency component represented by the eigenvector of each order obtained through the frequency analyzation, the eigenvector frequency component representing the blood flow signal indicates substantially the same high frequency without depending on the observed portion such as the carotid artery and the thyroid gland (see FIG. 9B). Thus, a stable blood flow extraction performance can be maintained even when the reduction rate of the eigenvector of each order is determined with reference to the same threshold (i.e., reference frequency) under a condition where the observed portion differs.

Note that while a mode in which reduction rate determination section 734 determines the reduction rate of the eigenvector of each order to be 0 or 1 is described above, reduction rate determination section 734 may determine the reduction rate of the eigenvector to be a value of 0 to 1 (note that fraction points are included) on the basis of the difference or the ratio between the reference frequency and the principal frequency component represented by the eigenvector. A plurality of eigenvectors calculated by principal component analysis execution section 731 includes an eigenvector representing a frequency component including both the clutter signal and the blood flow signal. For such an eigenvector, it is preferable that the reduction rate of the eigenvector be adjustable between 0 to 1, including fraction point, from the view point of achieving the high image quality of the ultrasound image.

Under the control of control section 9, MTI filter coefficient calculation section 732 calculates filter coefficient (i.e., MTI filter coefficient $A_{reg}$) of MTI filter 73 by Expression (2) from the gain matrix G input from reduction rate determination section 734 and the eigenvector input from principal component analysis execution section 731.

Under the control of control section 9, MTI filtering processing section 735 calculates packet data y as a complex Doppler signal by Expression (1) with the packet data x input from corner-turn control section 72 and the filter coefficient (i.e., MTI filter coefficient $A_{reg}$) input from MTI filter coefficient calculation section 732, and outputs the calculated packet data y to correlation computation section 74, as the Doppler signal I,Q of a blood flow component after the removal of the clutter signal.

Returning back to FIG. 3, a process of C-mode image generation section 7 (correlation computation section 74, data conversion section 75, noise removal space filter part 76, inter frame filter 77, and C-mode image conversion section 78) subsequent to the process of MTI filter 73 is described below.

Under the control of control section 9, correlation computation section 74 calculates real part D and imaginary part N of average value S (the average value of the phase difference vector) of the autocorrelation computation of the Doppler signal of the following Expression (7), from the Doppler signal I,Q (complex Doppler signal z) filtered by MTI filter 73.

[Math 4]

$$S = \sum_{k=0}^{n-1} z_k^* \cdot z_{k+1} = D + jN \qquad (7)$$

Under the control of control section 9, data conversion section 75 calculates blood flow velocity V, power P, and dispersion T, from the Doppler signal I,Q filtered by MTI filter 73 and real part D and imaginary part N of average value S of the autocorrelation computation of the Doppler signal. To be more specific, data conversion section 75 calculates blood flow velocity V by the following Expression (8) from real part D and imaginary part N of average value S of the autocorrelation computation of the Doppler signal.

[Math 5]

$$V = \tan^{-1} \frac{N}{D} \qquad (8)$$

In addition, data conversion section 75 calculates power P as the average value of the strength of the Doppler signal by the following Expression (9) from Doppler signal I,Q (complex Doppler signal z).

[Math 6]

$$P = \frac{1}{n} \sum_{k=0}^{n-1} |z_k|^2 \qquad (9)$$

In addition, data conversion section 75 calculates dispersion T as the ratio of the size of the phase difference vector and the power (note that, one subtracted from 1 and reversed in size) by the following Expression (10), from real part D and imaginary part N of average value S of the autocorrelation computation of the Doppler signal.

[Math 7]

$$T = 1 - \frac{\sqrt{D^2 + N^2}}{P} \qquad (10)$$

Noise removal space filter part 76 filters power P, blood flow velocity V and dispersion T calculated by data conversion section 75. Noise removal space filter part 76 includes a key hole filter and a space filter (which are not illustrated in the drawings), for example.

The key hole filter removes noise by filtering power P, blood flow velocity V, and dispersion T making up the frame of the C-mode image. In the V-mode and the V-T-mode, the key hole filter filters blood flow velocity V by removing blood flow velocity V of the region to be removed set by blood flow velocity V and power P calculated by data conversion section 75. In the V-mode and the V-T-mode, blood flow velocity V is used for the image display (coloring). In the P-mode, the key hole filter filters power P by removing power P of the region to be removed set by blood flow velocity V and power P calculated by data conversion section 75. In the P-mode, power P is used for the image display (coloring).

To be more specific, in the V-mode and the V-T-mode, the key hole filter regards the blood flow signal in the region where blood flow velocity V is smaller than a predetermined threshold, as clutter noise, and regards the blood flow signal in the region where power P is smaller than a predetermined threshold, as background noise, so as to remove the blood flow velocity V in these regions. In addition, in P-mode, the key hole filter regards the blood flow signal in the region where blood flow velocity V is smaller than a predetermined threshold, as clutter noise, and regards the blood flow signal in the region where power P is smaller than a predetermined threshold, as background noise, so as to remove power P in these regions.

The space filter is a two-dimensional weighted average filter for smoothing the data of blood flow velocity V, power P and dispersion T making up the frame of the C-mode image. In the V-mode or V-T-mode, the space filter filters the blood flow velocity V filtered by the key hole filter, and dispersion T calculated by data conversion section 75. In the P-mode, the space filter filters power P filtered by the key hole filter.

Inter frame filter 77 smoothens the inter frame variation and performs filtering so as to left an after-image (lag) for the blood flow component of each frame making up the C-mode image in accordance with the display mode operated and input at operation section 2 among blood flow velocity V, power P, and dispersion T filtered by noise removal space filter part 76.

By performing color mapping on blood flow velocity V, power P and dispersion T filtered by inter frame filter 77, C-mode image conversion section 78 converts it into the C-mode image data.

Returning back to FIG. 2, display processing section 8 performs a process of constructing display image data to be displayed on display section 11 and displaying the display image data on display section 11. In particular, in the case where B-mode is selected, a process of containing the B-mode image of the B-mode image data generated by B-mode image generation section 5 in the display image data, as the ultrasound image, is performed. In addition, in the case where C-mode is selected, a process of generating composite image data in which the C-mode image of the C-mode image data generated by C-mode image generation section 7 is superimposed at the position of selected ROI on the B-mode image generated by B-mode image generation section 5, as the ultrasound image, and containing it in the display image data, is performed.

Control section 9 includes, for example, a central processing unit (CPU), a read only memory (ROM), and a random access memory (RAM), reads various processing programs such as system programs stored in the ROM, loads it in the RAM, and controls the operation of each section of ultrasound diagnostic apparatus 1 in accordance with the loaded program. The RAM forms a work area for temporarily storing various programs to be executed by the CPU and data of the programs. The ROM is composed of non-volatile memory such as semiconductors and stores the system program for ultrasound diagnostic apparatus 1, various processing programs that can be executed on the system program, and various data. These programs are stored in the form of program codes that can be read by a computer, and the CPU sequentially executes operations according to the program codes.

For example, storage section 10 is composed of a large capacity recording medium such as a hard disk drive (HDD), and stores ultrasound image data (the B-mode image data, the C-mode image data, composite image data), and clutter removal table 110, frame rate table 120, the gain matrix and the frame rate described later, and the like.

Display section 11 is a monitor that displays the image data output from display processing section 8, such as so-called liquid crystal display (LCD) or electro luminescence (EL) display.

For each part of ultrasound diagnostic apparatus 1, some or all of the functions of each functional block may be implemented as hardware circuits such as integrated circuits. An integrated circuit is, for example, a large scale integration (LSI), which may also be called an integrated circuit (IC), System LSI, Super LSI, or Ultra LSI, depending on the degree of integration. The method of integrated circuits is not limited to LSI, but may be implemented by dedicated circuits or general-purpose processors, or by using field programmable gate array (FPGA) or reconfigurable processors that can reconfigure the connections and settings of circuit cells inside the LSI. In addition, some or all of the functions of each functional block may be performed by software. In this case, the software is stored on one or more ROM or other storage media, optical disk, or hard disk, and this software is executed by the processor.

Effect

As described above, in ultrasound diagnostic apparatus 1 according to the present embodiment, the principal frequency component represented by the eigenvector is calculated for each of a plurality of eigenvectors obtained by the principal component analysis of the reflection wave data group, and the reduction rate of reducing the eigenvector component from the ultrasound image is determined with reference to the principal frequency component represented by the eigenvector.

In this manner, the clutter component can be appropriately reduced from the packet data group (i.e., the time-series reflection wave data group in the region of interest, obtained at execution of the color flow mode) without depending on the size of blood flow information in the region of interest or the observed portion, and extraction of blood flow information with high S/N ratio can be achieved. In this manner, high image quality of ultrasound images can be achieved without the need for the user to set the filter characteristics of the MTI filter.

Second Embodiment

Figure 12:
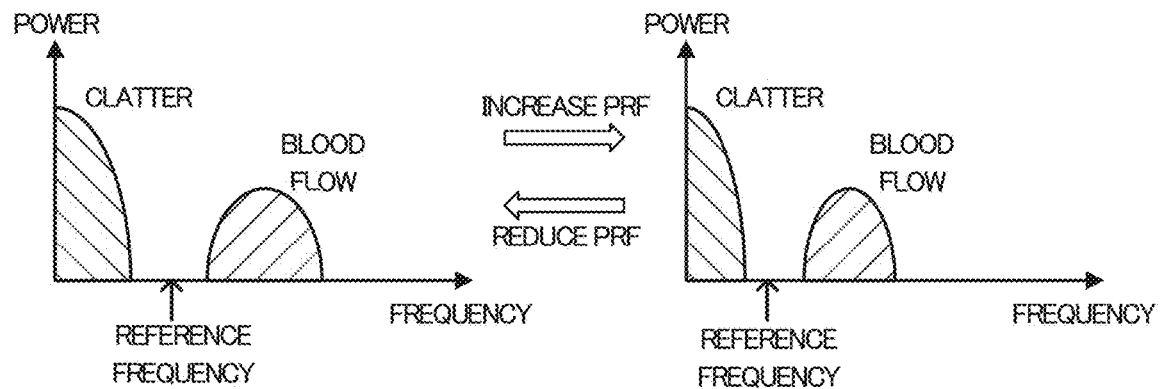
FIG. 12 is a diagram for describing a process of a reduction rate determination section according to a second embodiment.
Figure 13:
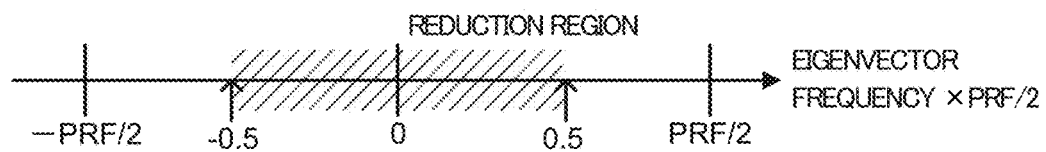
FIG. 13 is a diagram for describing another method of the process of the reduction rate determination section according to the second embodiment.

Next, with reference to FIG. 12 and FIG. 13, a configuration of ultrasound diagnostic apparatus 1 according to a second embodiment is described. Ultrasound diagnostic apparatus 1 according to the present embodiment differs from ultrasound diagnostic apparatus 1 according to the first embodiment in that reduction rate determination section 734 changes the setting of the clutter component reduction condition on the basis of the transmission/reception condition of the ultrasound at execution of the color flow mode (in this case, the repetition frequency of the ultrasound). Note that the description of the configurations common to the first embodiment is omitted (the same applies to other embodiments).

FIG. 12 is a diagram for describing an example of a process of reduction rate determination section 734 according to the present embodiment.

The setting of the repetition frequency of the ultrasound at execution of the color flow mode is appropriately changed on the basis of the types of the portion to be observed, the depth of the portion to be observed, the desired frame rate, and the like. It should be noted that in general, the Doppler deviation frequency that is obtained at execution of the color flow mode tends to be dependent on the repetition frequency of the ultrasound, and shifted to the high frequency side or the low frequency side as a whole (see FIG. 12). To be more specific, the Doppler deviation frequency is shifted to the low frequency side as a whole when the repetition frequency of the ultrasound is increased, whereas the Doppler deviation frequency is shifted to the high frequency side as a whole when the repetition frequency of the ultrasound is reduced.

The reason for this is that, in general, in ultrasound diagnostic apparatus 1, the measurement value of the Doppler deviation frequency (i.e., the measurement value of the blood flow velocity) is calculated as a value relative to the maximum observable flow velocity value defined by the transmission/reception condition of the ultrasound, and the maximum observable flow velocity value is proportional to the repetition frequency. Note that the maximum observable flow velocity Vmax is the critical velocity of the blood flow velocity at which the aliasing phenomenon (folding back) is not caused, and is calculated by the following publicly known Expression (11) from the transmission/reception condition of the ultrasound (i.e., the repetition frequency of the ultrasound, the transmission frequency of the ultrasound) for example.

$$V\max = c \times ft/(4 \times fs) \times 10^{-1} \qquad (11)$$

(note that Vc [cm/s]: the maximum observable flow velocity, c [m/s]: the velocity of sound in the specimen ultrasound, ft

[kHz]: the critical frequency of pulse repetition frequency, and fs [MHz]: the transmission frequency of the ultrasound beam)

That is, here, the maximum observable flow velocity Vmax is set to "1.0" of the above-mentioned Expression (6), for example. Then, the measurement value of the blood flow velocity (i.e., the measurement value of the Doppler deviation frequency) is set on the axis of the frequency normalized by the transmission/reception condition of the ultrasound (i.e., the repetition frequency of the ultrasound, and the transmission frequency of the ultrasound).

Under such a circumstance, the frequency component of the clutter signal and the frequency component of the blood flow signal are also dependent on the repetition frequency of the ultrasound and changed to the high frequency side or the low frequency side as a whole. At this time, if the reduction rate of the eigenvector is determined without taking into account the repetition frequency of the ultrasound, a large amount of the clutter component may remain in the blood flow image, or conversely, the blood flow component may be excessively removed from the blood flow image.

From such a viewpoint, reduction rate determination section 734 according to the present embodiment changes the setting of the clutter component reduction condition such that the lower the repetition frequency of the ultrasound at execution of the color flow mode, the more the reference frequency (i.e., the frequency for identifying the blood flow component and the clutter component) is shifted to the high frequency side.

To be more specific, reduction rate determination section 734 according to the present embodiment changes the setting of the reference frequency on the basis of the repetition frequency of the ultrasound at execution of the color flow mode, and typically, changes the setting such that the lower the repetition frequency of the ultrasound at execution of the color flow mode, the more the reference frequency is set to the high frequency side (see FIG. 12). Note that storage section 10 preliminarily stores the correction data for shift correction of the reference frequency by the deviation amount of the repetition frequency of the ultrasound from the standard value at execution of the color flow mode, and reduction rate determination section 734 sets the reference frequency by using the correction data. Then, reduction rate determination section 734 determines the reduction rate by using the reference frequency after the correction for the eigenvector of each order.

In this manner, the reduction rate of the eigenvector can be appropriately determined in accordance with the frequency band of the clutter component and the frequency band of the blood flow component that change in linkage with the repetition frequency of the ultrasound.

Note that at this time, reduction rate determination section 734 according to the present embodiment may correct the eigenvector frequency instead of/together with correction of the reference frequency. FIG. 13 is a diagram for describing another method of a process of reduction rate determination section 734 according to the present embodiment. For example, in FIG. 13, the value of the reference frequency is "0.5" without change, and the value of the frequency of the eigenvector is converted to the value of "eigenvector frequency x the repetition frequency of the ultrasound (in this case, PRF/2)". Here, the value of "the repetition frequency of the ultrasound" for multiplying the eigenvector frequency for multiplying the eigenvector frequency is a normalization value, and is set on the large side or the small side with respect to "1.0" by the deviation amount of the repetition frequency from the standard value at execution of the color flow mode, with the standard value of the repetition frequency set to "1.0" for example.

Also with this method, as described above, the setting of the clutter component reduction condition is changed such that the lower the repetition frequency of the ultrasound at execution of the color flow mode, the more the reference frequency is relatively shifted to the high frequency side.

In this manner, with ultrasound diagnostic apparatus 1 according to the present embodiment, the reduction rate of the eigenvector can be appropriately determined on the basis of the transmission/reception condition of the ultrasound at execution of the color flow mode (in this case, the repetition frequency of the ultrasound), and thus the quality of the ultrasound image image can be further improved.

Third Embodiment

Figure 14:
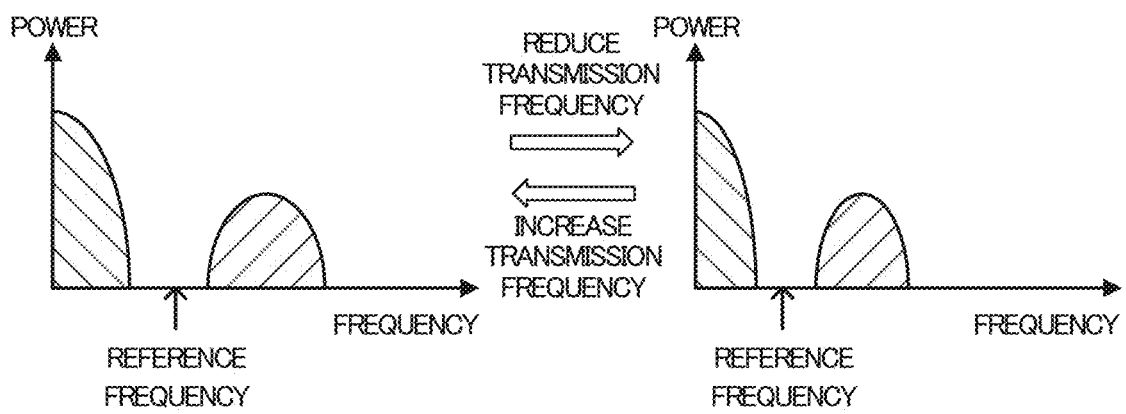
FIG. 14 is a diagram for describing a process of a reduction rate determination section according to a third embodiment.
Figure 15:
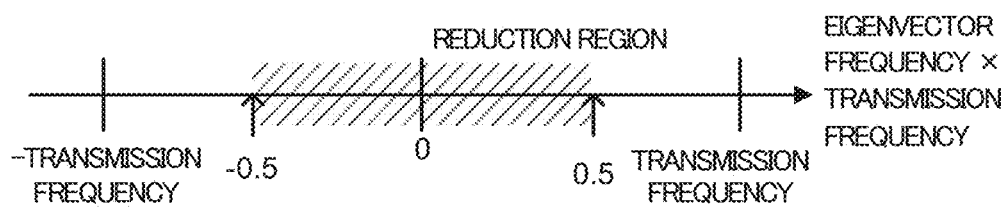
FIG. 15 is a diagram for describing another method of the process of the reduction rate determination section according to the third embodiment.

Next, with reference to FIG. 14 and FIG. 15, a configuration of ultrasound diagnostic apparatus 1 according to a third embodiment is described. Ultrasound diagnostic apparatus 1 according to the present embodiment differs from ultrasound diagnostic apparatus 1 according to the first embodiment in that reduction rate determination section 734 automatically changes the setting of the clutter component reduction condition on the basis of the transmission/reception condition of the ultrasound at execution of the color flow mode (in this case, the transmission frequency of the ultrasound). Note that reduction rate determination section 734 according to the present embodiment is designed under the same design concept as reduction rate determination section 734 described in the second embodiment.

FIG. 14 is a diagram for describing an example of a process of reduction rate determination section 734 according to the present embodiment.

The setting of the transmission frequency of the ultrasound at execution of the color flow mode is appropriately changed on the basis of the types of the portion to be observed, the depth of the portion to be observed, the desired frame rate, and the like. It should be noted that in general, the Doppler deviation frequency that is obtained at execution of the color flow mode tends to be dependent on the transmission frequency of the ultrasound, and shifted to the high frequency side or the low frequency side as a whole (see FIG. 14). To be more specific, the Doppler deviation frequency is shifted to the high frequency side as a whole when the transmission frequency of the ultrasound is increased, and the Doppler deviation frequency is shifted to the low frequency side as a whole when the transmission frequency of the ultrasound is reduced.

The reason for this is that, in general, in ultrasound diagnostic apparatus 1, the measurement value of the Doppler deviation frequency (i.e., the measurement value of the blood flow velocity) is calculated as a value relative to the maximum observable flow velocity value defined by the transmission/reception condition of the ultrasound, and the maximum observable flow velocity value is proportional to the inverse of the transmission frequency.

Note that the relationship between the maximum observable flow velocity value and transmission frequency is as described above with reference to Expression (11). In Expression (11), the transmission frequency of the ultrasound beam is a frequency of a burst wave that is transmitted as an ultrasound beam. In the pulse Doppler mode, the Doppler deviation frequency is calculated from the phase difference between nth transmission wave and the n+first transmission wave. Therefore, as the transmission frequency of the ultrasound beam increases, the resolution of the Doppler deviation frequency increases, while the maximum observable flow velocity value decreases.

Under such a circumstance, the frequency component of the clutter signal and the frequency component of the blood flow signal are dependent on the transmission frequency of the ultrasound, and are changed to the high frequency side or the low frequency side as a whole.

From such a viewpoint, reduction rate determination section 734 according to the present embodiment changes the setting of the clutter component reduction condition such that the lower the transmission frequency of the ultrasound at execution of the color flow mode, the more the reference frequency (i.e., the frequency for identifying the blood flow component and the clutter component) is shifted to the low frequency side.

To be more specific, reduction rate determination section 734 according to the present embodiment changes the setting of the reference frequency set to the clutter component reduction condition on the basis of the transmission frequency of the ultrasound at execution of the color flow mode, and typically changes the setting such that the lower the transmission frequency of the ultrasound low at execution of the color flow mode, the more the reference frequency is set to the low frequency side (see FIG. 14). Note that storage section 10 preliminarily stores correction data for shift correction of the reference frequency by the deviation amount of the transmission frequency of the ultrasound at execution of the color flow mode from the standard frequency, and reduction rate determination section 734 sets the reference frequency by using the correction data. Then, reduction rate determination section 734 determines the reduction rate by using the reference frequency after the correction the eigenvector of each order.

In this manner, the reduction rate of the eigenvector can be appropriately determined in accordance with the frequency band of the clutter component and the frequency band of the blood flow component that change in linkage with the transmission frequency of the ultrasound.

Note that at this time, reduction rate determination section 734 according to the present embodiment may correct the eigenvector frequency instead of/together with correction of the reference frequency. FIG. 15 is a diagram for describing another method of a process of reduction rate determination section 734 according to the present embodiment. For example, in FIG. 15, the value of the frequency of the eigenvector is converted to the value of "eigenvector frequency x transmission frequency", with the value of the reference frequency set to "0.5" without change. Here, the value of "transmission frequency" for multiplying the eigenvector frequency is a normalization value, and is set on the large side or the small side with respect to "1.0" by the deviation amount of the transmission frequency from the standard value at execution of the color flow mode, with the transmission frequency set to the standard value "1.0", for example.

Also with this method, as described above, the setting of the clutter component reduction condition is changed such that the lower the transmission frequency of the ultrasound at execution of the color flow mode, the more the reference frequency is relatively shifted to the high frequency side.

In this manner, with ultrasound diagnostic apparatus 1 according to the present embodiment, the reduction rate of the eigenvector can be appropriately determined on the basis of the transmission/reception condition of the ultrasound at execution of the color flow mode (in this case, the transmission frequency of the ultrasound), and thus the quality of the ultrasound image can be further improved.

Fourth Embodiment

Figure 16:
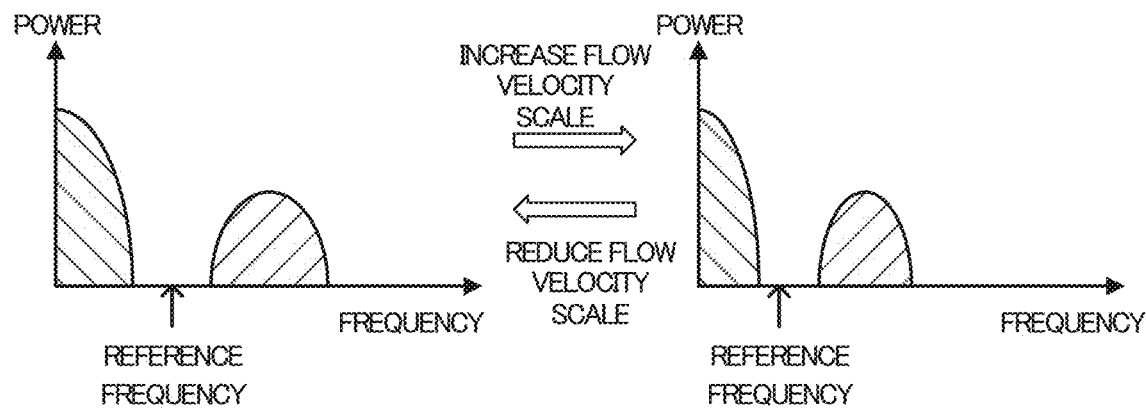
FIG. 16 is a diagram for describing a process of a reduction rate determination section according to a fourth embodiment.
Figure 17:
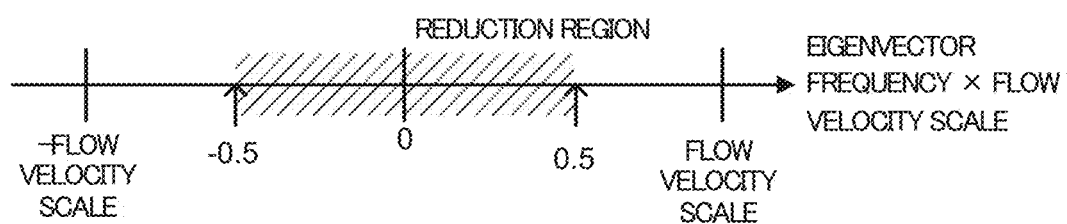
FIG. 17 is a diagram for describing another method of a process of the reduction rate determination section according to the fourth embodiment.

Next, with reference to FIG. 16 and FIG. 17, a configuration of ultrasound diagnostic apparatus 1 according to a fourth embodiment is described. Ultrasound diagnostic apparatus 1 according to the present embodiment differs from ultrasound diagnostic apparatus 1 according to the first embodiment in that reduction rate determination section 734 automatically changes the setting of the clutter component reduction condition on the basis of the transmission/reception condition of the ultrasound at execution of the color flow mode (in this case, the flow velocity scale of the observation object). Note that reduction rate determination section 734 according to the present embodiment is designed under the same design concept as reduction rate determination section 734 described in the second embodiment.

FIG. 16 and FIG. 17 are diagrams for describing the clutter component reduction condition of reduction rate determination section 734 according to the present embodiment.

The flow velocity scale defines the range and the resolution of the displayable blood flow velocity, and is manually set by the user, or automatically set based on the blood flow velocity during a predetermined period. Typically, the setting information of the flow velocity scale is automatically reflected to the pulse repetition frequency of transmission of an ultrasound beam corresponding to the sampling frequency. To be more specific, in the case where the flow velocity scale is set in a low velocity scale range (i.e., the range of the observation object is only low velocity), the pulse repetition frequency is set to low frequency, and whereas in the case where the flow velocity scale is set in a high velocity scale range (i.e., the range of the observation object includes low velocity and high velocity), the pulse repetition frequency is set to high frequency. Note that such a process is typically performed by control section 9.

As described above, the flow velocity scale setting sets the pulse repetition frequency, and therefore in general, the Doppler deviation frequency that is obtained at execution of the color flow mode tends to be dependent on the flow velocity scale setting and shifted to the high frequency side or the low frequency side as a whole (see FIG. 16). To be more specific, in general, in the case where the flow velocity scale setting is increased, the Doppler deviation frequency is shifted to the low frequency side as a whole when the flow velocity scale setting is in the high velocity scale range (i.e., wide scale), whereas the Doppler deviation frequency is shifted to the high frequency side as a whole when the flow velocity scale setting is in the low velocity scale range.

From such a viewpoint, reduction rate determination section 734 according to the present embodiment as in the second embodiment changes the setting of the reference frequency set to the clutter component reduction condition on the basis of the flow velocity scale setting at execution of the color flow mode, and typically changes the setting such that the lower the velocity scale range of the flow velocity scale setting at execution of the color flow mode, the more the reference frequency is on the high frequency side (see FIG. 16). Note that storage section 10 preliminarily stores correction data for shift correction of the reference frequency by the deviation amount of the flow velocity scale setting at execution of the color flow mode from the standard scale, and reduction rate determination section 734 sets the reference frequency by using the correction data. Then, reduction rate determination section 734 determines the reduction rate by using the reference frequency after the correction the eigenvector of each order.

In this manner, the reduction rate of the eigenvector can be appropriately determined in accordance with the frequency band of the clutter component and the frequency band of the blood flow component that change in linkage with the flow velocity scale setting.

Note that at this time, reduction rate determination section 734 according to the present embodiment may correct the eigenvector frequency instead of/together with correction of the reference frequency. FIG. 17 is a diagram for describing another method of a process of reduction rate determination section 734 according to the present embodiment. For example, in FIG. 17, the value of the frequency of the eigenvector is converted to the value of "eigenvector frequency x the flow velocity scale setting", with the value of the reference frequency set to "0.5" without change. Here, the value of "the flow velocity scale setting" for multiplying the eigenvector frequency is a normalization value, and is set on the large side or the small side with respect to "1.0" by the deviation amount of the flow velocity scale setting from the standard value at execution of the color flow mode with the standard value of the flow velocity scale setting set to "1.0", for example.

Also with this method, as described above, the setting of the clutter component reduction condition is changed such that the lower the velocity scale range of the flow velocity scale setting at execution of the color flow mode, the more the reference frequency is relatively shifted to the high frequency side.

As described above, with ultrasound diagnostic apparatus 1 according to the present embodiment, the reduction rate of the eigenvector can be appropriately determined based on the transmission/reception condition of the ultrasound at execution of the color flow mode (in this case, the flow velocity scale setting), and thus the quality of the ultrasound image can be further improved.

Fifth Embodiment

Figure 18:
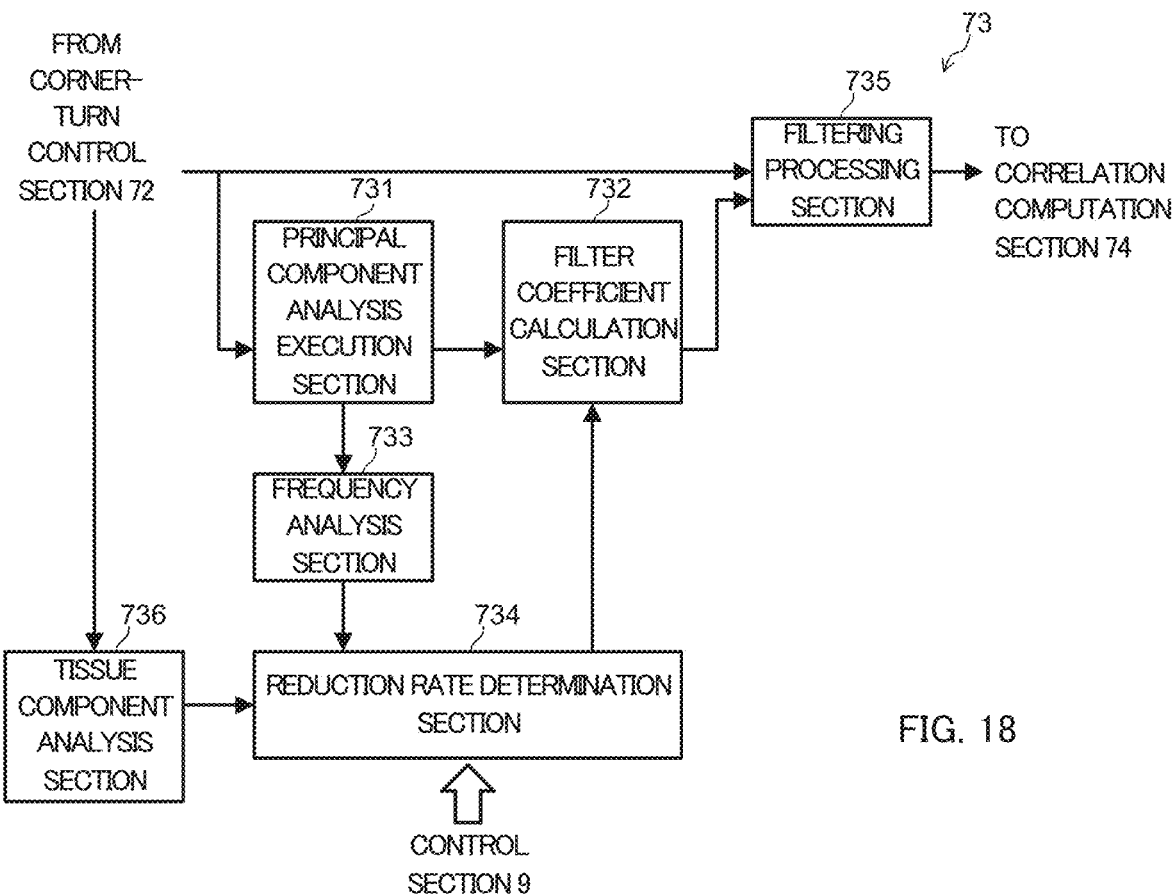
FIG. 18 is a diagram illustrating an internal configuration of an MTI filter according to a fifth embodiment.
Figure 19:
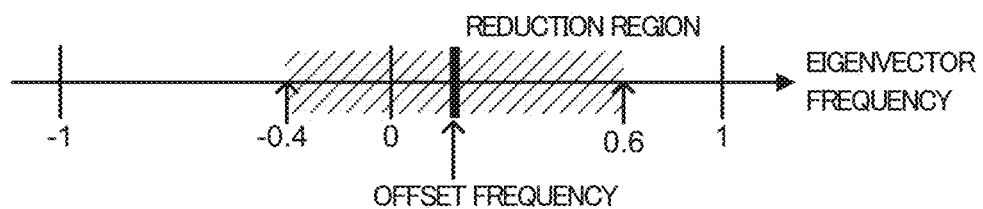
FIG. 19 is a diagram for describing a process of the reduction rate determination section according to the fifth embodiment.

Next, with reference to FIG. 18 and FIG. 19, a configuration of ultrasound diagnostic apparatus 1 according to a fifth embodiment is described.

FIG. 18 is a diagram illustrating an internal configuration of MTI filter 73 according to the present embodiment. FIG. 19 is a diagram for describing a process of reduction rate determination section 734 according to the present embodiment.

Ultrasound diagnostic apparatus 1 according to the present embodiment differs from ultrasound diagnostic apparatus 1 according to the first embodiment in that tissue component analysis section 736 that analyzes the frequency band where the clutter component appears on the basis of time-series reflection wave data group is provided, and that reduction rate determination section 734 automatically changes the setting of the clutter component reduction condition so as to offset the frequency band of the reference frequency on the basis of the frequency band where the clutter component appears.

The blood vessel under observation does not necessarily exist completely independent of the tissue structure (e.g., heart) from which the clutter component originates, but often exists on such tissue structure in conjunction with such tissue structure. In such cases, the blood flow in the vessel to be observed is superimposed on the movement of such tissue structures, and the Doppler signal from the blood flow will be Doppler shifted by the velocity of the movement of such tissue structures. Therefore, the frequency band of the eigenvector representing the blood flow calculated by principal component analysis is also shifted by the velocity of the movement of the tissue structure.

From such a viewpoint, in ultrasound diagnostic apparatus 1 according to the present embodiment, the reference frequency (i.e., the frequency for identifying the blood flow component and the clutter component) is offset by the velocity corresponding to the movement of the tissue structure that overlaps the blood vessel under observation (see FIG. 19).

To be more specific, tissue component analysis section 736 acquires the time-series reflection wave data group obtained in the blood flow region of the observation object at execution of the color flow mode, from corner-turn control section 72. Then, tissue component analysis section 736 calculates the frequency component included in the blood flow region of the observation object by performing publicly known frequency analysis using FFT, autocorrelation computation and the like on the time-series reflection wave data group obtained in the blood flow region of the observation object, and thus obtains the frequency component of the clutter component in the blood flow region of the observation object. Note that at this time, tissue component analysis section 736 may estimate the frequency component of low frequency band with the strongest signal strength in the frequency component included in the blood flow region of the observation object as the frequency component of the clutter component, or may estimate the average frequency of the frequency component included in the blood flow region of the observation object as the frequency component of the clutter component, for example.

Reduction rate determination section 734 offsets the frequency band of the reference frequency on the basis of the frequency component of the clutter component estimated by tissue component analysis section 736 (see FIG. 19). Note that storage section 10 preliminarily stores correction data for shift correction of the reference frequency in association with the frequency component of the clutter component, and reduction rate determination section 734 sets the reference frequency by using the correction data. For example, FIG. 19 illustrates a mode where reduction rate determination section 734 changes the setting such that the reference frequency is set to a value "0.6" offset by the frequency component "0.1" of the clutter component from the initial value "0.5". Then, reduction rate determination section 734 determines the reduction rate of the eigenvector of each order by using the reference frequency after the offset.

As described above, with ultrasound diagnostic apparatus 1 according to the present embodiment, the reduction rate of the eigenvector can be appropriately determined by offsetting the frequency band of the reference frequency on the basis of the frequency band of the clutter component in the blood flow region of the observation object. In this manner, the quality of the ultrasound image can be further improved.

Note that the time-series reflection wave data group for which the frequency analysis is performed at tissue component analysis section 736 is typically a reflection wave data group obtained in the ROI region at execution of the color flow mode (i.e., the reflection wave data group used by the principal component analysis execution section 731 for the principal component analysis). It should be noted that the reflection wave data group need not necessarily be one that is obtained at the same timing as the reflection wave data group that is used by principal component analysis execution section 731 for the principal component analysis. For example, the reflection wave data group may be a reflection wave data group obtained a tick earlier than the reflection wave data group used by principal component analysis execution section 731 for the principal component analysis.

Sixth Embodiment

Figure 20:
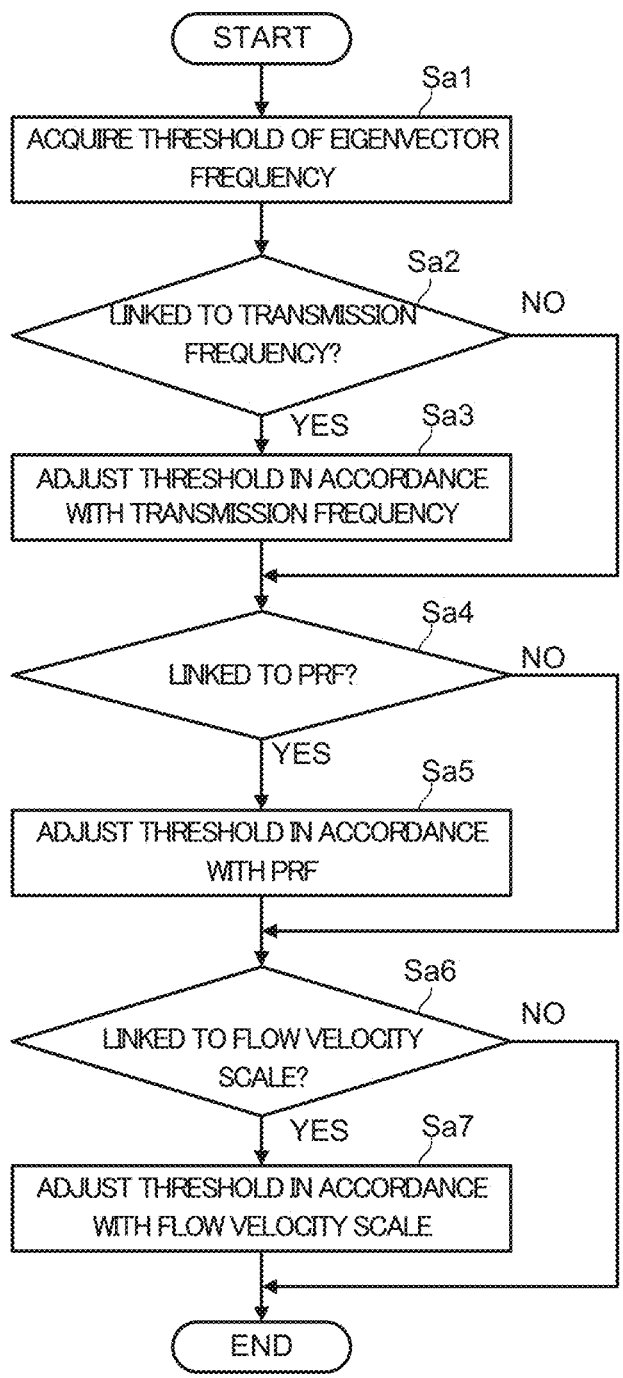
FIG. 20 is a diagram for describing an operation procedure of an ultrasound diagnostic apparatus according to a sixth embodiment.
Figure 21:
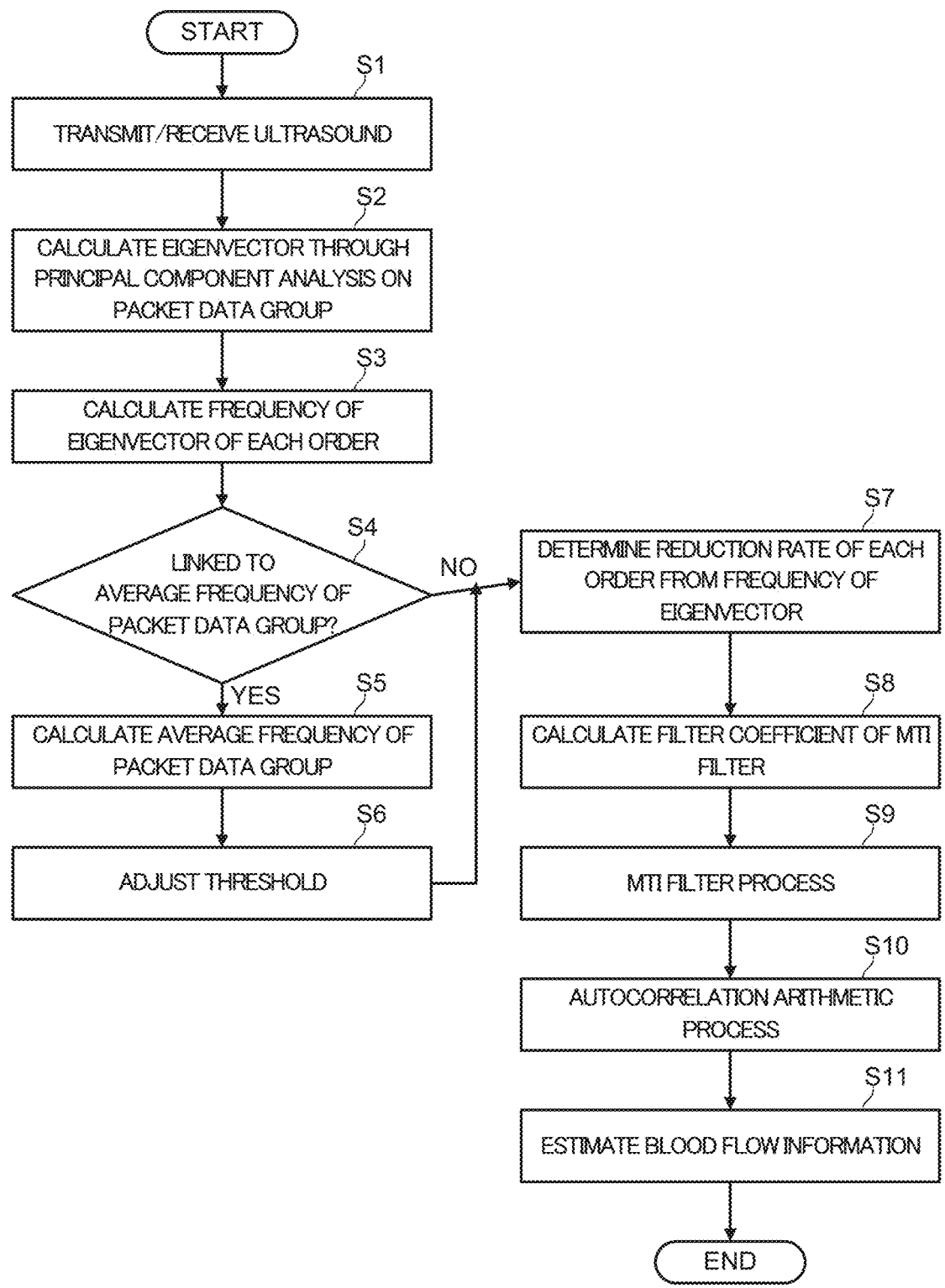
FIG. 21 is a diagram for describing an operation procedure of the ultrasound diagnostic apparatus according to the sixth embodiment.
Figure 22:
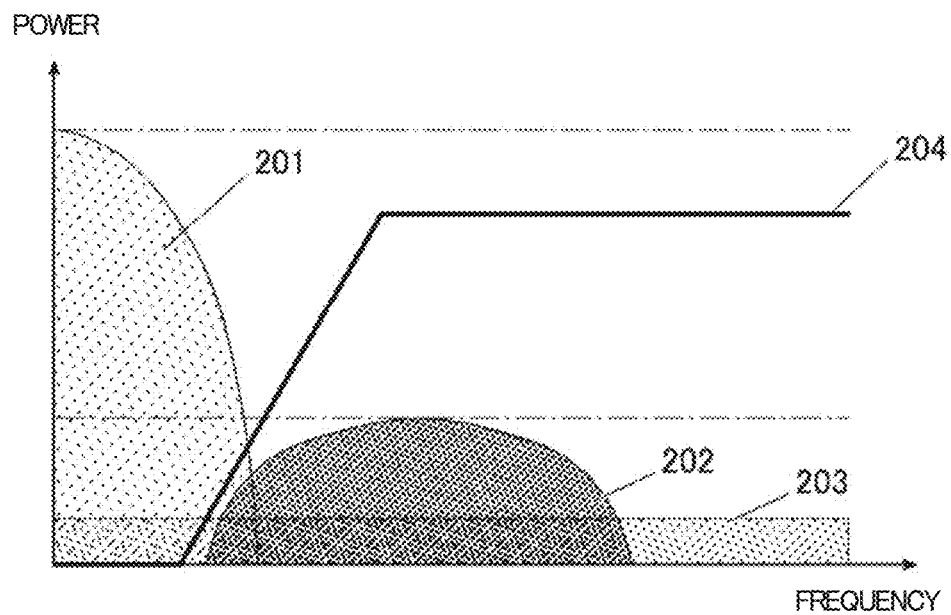
FIG. 22 is frequency characteristics of a power of a filter of a known moving target indication (MTI).

Next, with reference to FIG. 20 and FIG. 21, a configuration of ultrasound diagnostic apparatus 1 according to a sixth embodiment is described.

Ultrasound diagnostic apparatus 1 according to the present embodiment has all automatic setting functions of the reference frequency described in the second to fifth embodiments for the purpose of setting a more accurate value to the reference frequency. It should be noted that the transmission frequency of the ultrasound, the repetition frequency of the ultrasound, and the flow velocity scale setting may be automatically set in linkage with each other depending on the operation setting of ultrasound diagnostic apparatus 1. Therefore, ultrasound diagnostic apparatus 1 according to the present embodiment is configured to be switchable between valid or invalid of the automatic setting functions through the user operation. Note that the setting information regarding the valid or invalid of the automatic setting functions is stored in storage section 10, for example.

FIG. 20 and FIG. 21 are diagrams for describing an operation procedure of ultrasound diagnostic apparatus 1 according to the present embodiment. Note that it is assumed here that the valid or invalid of the automatic setting function of the reference frequency described in the second to fifth embodiments has been set through user operation.

FIG. 20 is a diagram illustrating a process of setting the threshold that sets the rank cut order (i.e., reference frequency) by ultrasound diagnostic apparatus 1 according to the present embodiment at first at execution of the color flow mode on the basis of the transmission/reception condition of the ultrasound.

At step Sa1, ultrasound diagnostic apparatus 1 (reduction rate determination section 734) acquires the threshold of the eigenvector frequency from storage section 10. Note that the threshold acquired at this time means the initial value before adjustment and corresponds to "0.5" in FIG. 8.

At step Sa2, ultrasound diagnostic apparatus 1 (reduction rate determination section 734) determines whether to link the threshold that sets the rank cut order to the transmission frequency on the basis of the setting information of the user. Then, when the threshold is linked to the transmission frequency (Sa2: YES), the process is advanced to step Sa3, and when the threshold is not linked to transmission frequency (Sa2: NO), the process is advanced to step Sa4.

At step Sa3, ultrasound diagnostic apparatus 1 (reduction rate determination section 734) adjusts the threshold in accordance with the transmission frequency of the ultrasound at execution of the color flow mode. Note that at this time, ultrasound diagnostic apparatus 1 (reduction rate determination section 734) operates such that the lower the transmission frequency of the ultrasound at execution of the color flow mode, the lower the threshold is shifted and corrected to the low frequency side.

At step Sa4, ultrasound diagnostic apparatus 1 (reduction rate determination section 734) determines whether to link the threshold that sets the rank cut order to the repetition frequency of the ultrasound (RPF) on the basis of the setting information of the user. Then, when the threshold is linked to the repetition frequency of the ultrasound (Sa4: YES), the process is advanced to step Sa5, and, when the threshold is not linked to the repetition frequency of the ultrasound (Sa4: NO), the process is advanced to step Sa6.

At step Sa5, ultrasound diagnostic apparatus 1 (reduction rate determination section 734) adjusts the threshold in accordance with the repetition frequency of the ultrasound at execution of the color flow mode. Note that at this time, ultrasound diagnostic apparatus 1 (reduction rate determination section 734) operates such that the lower the repetition frequency of the ultrasound at execution of the color flow mode, the more the threshold is shifted and corrected to the high frequency side.

At step Sa6, ultrasound diagnostic apparatus 1 (reduction rate determination section 734) determines whether to link the threshold that sets the rank cut order to the flow velocity scale on the basis of the setting information of the user. Then, when the threshold is linked to the flow velocity scale (Sa6: YES), the process is advanced to step Sa1, and, when the threshold is not linked to the flow velocity scale (Sa6: NO), the process of the flowchart of FIG. 20 is terminated.

At step Sa1, ultrasound diagnostic apparatus 1 (reduction rate determination section 734) adjusts the threshold in accordance with the flow velocity scale at execution of the color flow mode. Note that at this time, ultrasound diagnostic apparatus 1 (reduction rate determination section 734) operates such that the lower the velocity scale range of the flow velocity scale at execution of the color flow mode, the more the threshold is shifted and corrected to the high frequency side.

FIG. 21 is a diagram illustrating a process that is executed by ultrasound diagnostic apparatus 1 according to the present embodiment every time when generating each frame of a blood flow image during execution of the color flow mode.

At step S1, at execution of the color flow mode, ultrasound diagnostic apparatus 1 performs ultrasound scanning within the region of interest while performing the transmission and reception of ultrasound in the same direction multiple times. Then, the time-series reflection wave data group received in this manner is acquired as the analysis object of the principal component analysis (i.e., packet data group).

At step S2, ultrasound diagnostic apparatus 1 (principal component analysis execution section 731) calculates the eigenvector by performing the principal component analysis on the packet data group acquired at step S1 (i.e., the eigenvalue problem for the covariance matrix R is solved).

At step S3, ultrasound diagnostic apparatus 1 (frequency analysis section 733) calculates the principal frequency component represented by the eigenvector of each order by using the above-mentioned Expression (5) and Expression (6).

At step S4, ultrasound diagnostic apparatus 1 (reduction rate determination section 734) determines whether to link the threshold that sets the rank cut order to the average frequency of the packet data group (i.e., clutter component) on the basis of the setting information of the user. Then, when the threshold is linked to the average frequency of the packet data group (i.e., the frequency band of the clutter component) (S4: YES), the process is advanced to step S5, and, when the threshold is not linked to the average frequency of the packet data group (i.e., the frequency band of the clutter component) (S4: NO), the process is advanced to step S7.

At step S5, ultrasound diagnostic apparatus 1 (tissue component analysis section 736) calculates the average frequency of the packet data group (i.e., the frequency band of the clutter component).

At step S6, ultrasound diagnostic apparatus 1 (reduction rate determination section 734) adjusts the threshold on the basis of the average frequency of the packet data group calculated at step S5. Note that the threshold that is referred to at step S6 is the threshold that has been set in the process of the flowchart of FIG. 20.

At step S7, ultrasound diagnostic apparatus 1 (reduction rate determination section 734) determines the reduction rate of the eigenvector of each order from the frequency of the eigenvector on the basis of the threshold.

At step S8, ultrasound diagnostic apparatus 1 (filter coefficient calculation section 732) calculates the filter coefficient of MTI filter 73 by using the above-mentioned Expression (2) with reference to the reduction rate of the eigenvector of each order determined at step S7.

At step S9, ultrasound diagnostic apparatus 1 (filtering processing section 735) performs filtering process on the packet data group acquired at step S1 by using the above-mentioned Expression (1) with reference to MTI filter 73 calculated at step S8, and sets the calculated packet data group as a Doppler signal of the blood flow component after the removal of the clutter signal.

At step S10, ultrasound diagnostic apparatus 1 (correlation computation section 74) performs an autocorrelation arithmetic process on the Doppler signal obtained at step S9.

At step S11, ultrasound diagnostic apparatus 1 (data conversion section 75, noise removal space filter part 76, inter frame filter 77, and C-mode image conversion section 78) estimates the blood flow information on the basis of the Doppler signal obtained at step S10.

Through the above-described process, ultrasound diagnostic apparatus 1 according to the present embodiment can generate a blood flow image with high image quality.

As described above, with ultrasound diagnostic apparatus 1 according to the present embodiment, the reduction rate of the eigenvector can be appropriately determined on the basis of the transmission/reception condition of the ultrasound at execution of the color flow mode and the like, and thus the quality of the ultrasound image image can be further improved.

Although embodiments of the embodiment of the present invention have been described and illustrated in detail, the disclosed embodiments are made for purpose of illustration and example only and not limitation. The scope of the embodiment of the present invention should be interpreted by terms of the appended claims.

INDUSTRIAL APPLICABILITY

The ultrasound diagnostic apparatus according to the embodiment of the present disclosure can automatically set appropriate MTI filter characteristics.

REFERENCE SIGNS LIST

1 Ultrasound diagnostic apparatus
2 Operation section
3 Transmission section
4 Reception section
5 B-mode image generation section
6 ROI setting section
7 C-mode image generation section
8 Display processing section
9 Control section
10 Storage section
71 Orthogonal detection circuit
72 Corner-turn control section
73 MTI filter
731 Principal component analysis execution section
732 Filter coefficient calculation section
733 Frequency analysis section
734 Reduction rate determination section
735 Filtering processing section
736 Tissue component analysis section
74 Correlation computation section
75 Data conversion section
76 Noise removal space filter part
77 Inter frame filter
78 C-mode image conversion section
100 Ultrasound diagnostic apparatus main body
101 Ultrasound probe
101a Transducer

What is claimed is:

1. An ultrasound diagnostic apparatus that transmits ultrasound toward an inside of a specimen and receives a reflection wave therefrom to generate a blood flow image of the specimen, the ultrasound diagnostic apparatus comprising a hardware processor configured to:
   calculate a plurality of eigenvectors by performing principal component analysis on a time-series reflection wave data group in a predetermined region in the specimen obtained at execution of a color flow mode;
   calculate a principal frequency component of a time direction represented by the plurality of eigenvectors by performing frequency analyzation on each of the plurality of eigenvectors, the principal frequency component of the each of the plurality of eigenvectors is an average frequency of time variation of an observation object position represented by the each of the plurality of eigenvectors;
   determine a reduction rate of each of the plurality of eigenvectors on a basis of the principal frequency component of each of the plurality of eigenvectors and a clutter component reduction condition that defines a reference frequency for reduction of a clutter component;
   calculate a filter coefficient for reduction of the clutter component on a basis of the plurality of eigenvectors, and the reduction rate corresponding to each of the plurality of eigenvectors; and
   generate blood flow image data by applying the filter coefficient to the time-series reflection wave data group.

2. The ultrasound diagnostic apparatus according to claim 1,
   wherein the hardware processor is configured to determine the reduction rate of the eigenvector to be 0 when the principal frequency component of the eigenvector is greater than the reference frequency; and
   wherein the hardware processor is configured to determine the reduction rate of the eigenvector to be 1 when the principal frequency component of the eigenvector is smaller than the reference frequency.

3. The ultrasound diagnostic apparatus according to claim 1, wherein the hardware processor is configured to determine the reduction rate of the eigenvector to be a value of 0 to 1 including fraction points on a basis of a difference or a ratio between the principal frequency component of the eigenvector and the reference frequency.

4. The ultrasound diagnostic apparatus according to claim 1, wherein the hardware processor is configured to calculate the principal frequency component of the eigenvector on a basis of an autocorrelation value of the eigenvector.

5. The ultrasound diagnostic apparatus according to claim 1, wherein the hardware processor is configured to change a setting of the clutter component reduction condition to shift the reference frequency to a high frequency side or a low frequency side on a basis of a transmission/reception condition of ultrasound at execution of the color flow mode.

6. The ultrasound diagnostic apparatus according to claim 5, wherein the transmission/reception condition of ultrasound includes a transmission frequency of ultrasound.

7. The ultrasound diagnostic apparatus according to claim 5, wherein the transmission/reception condition of ultrasound includes a repetition frequency of ultrasound.

8. The ultrasound diagnostic apparatus according to claim 5, wherein the transmission/reception condition of ultrasound includes a flow velocity scale setting.

9. The ultrasound diagnostic apparatus according to claim 5,
wherein the hardware processor configured to analyze a frequency band of the clutter component on a basis of the time-series reflection wave data group in the predetermined region in the specimen obtained at execution of the color flow mode; and
wherein the hardware processor is configured to change the setting of the clutter component reduction condition to offset the reference frequency on a basis of the frequency band of the clutter component.

10. The ultrasound diagnostic apparatus according to claim 5,
wherein the hardware processor is configured to change the clutter component reduction condition on a basis of first information about a transmission frequency of ultrasound, second information about a repetition frequency of ultrasound, a third information about a flow velocity scale setting, and fourth information about a frequency band where the clutter component appears, at execution of the color flow mode; and
wherein the hardware processor is configured to determine valid or invalid of each of the first to fourth information as information that is referred to when changing the clutter component reduction condition, on a basis of a setting operation for each of the first information to fourth information by a user.

11. The ultrasound diagnostic apparatus according to claim 1, wherein the hardware processor is configured to adjust the reference frequency on a basis of a setting operation of a user.

12. A control method of an ultrasound diagnostic apparatus that transmits ultrasound toward an inside of a specimen and receives a reflection wave therefrom to generate a blood flow image of the specimen, the control method comprising:
a first process of calculating a plurality of eigenvectors by performing principal component analysis on a time-series reflection wave data group in a predetermined region in the specimen obtained at execution of a color flow mode;
a second process of calculating a principal frequency component of a time direction represented by the plurality of eigenvectors by performing analyzation on each of the plurality of eigenvectors, the principal frequency component of the each of the plurality of eigenvectors is an average frequency of time variation of an observation object position represented by the each of the plurality of eigenvectors;
a third process of determining a reduction rate of each of the plurality of eigenvectors on a basis of the principal frequency component of each of the plurality of eigenvectors and a clutter component reduction condition that defines a reference frequency for reduction of a clutter component;
a fourth process of calculating a filter coefficient for reduction of the clutter component on a basis of the plurality of eigenvectors, and the reduction rate corresponding to each of the plurality of eigenvectors; and
a fifth process of generating blood flow image data by applying the filter coefficient to the time-series reflection wave data group.

13. A non-transitory computer-readable recording medium storing a control program of an ultrasound diagnostic apparatus that transmits ultrasound toward an inside of a specimen and receives a reflection wave therefrom to generate a blood flow image of the specimen, the control program comprising:
a first process of calculating a plurality of eigenvectors by performing principal component analysis on a time-series reflection wave data group in a predetermined region in the specimen obtained at execution of a color flow mode;
a second process of calculating a principal frequency component of a time direction represented by the plurality of eigenvectors by performing analyzation on each of the plurality of eigenvectors, the principal frequency component of the each of the plurality of eigenvectors is an average frequency of time variation of an observation object position represented by the each of the plurality of eigenvectors;
a third process of determining a reduction rate of each of the plurality of eigenvectors on a basis of the principal frequency component of each of the plurality of eigenvectors and a clutter component reduction condition that defines a reference frequency for reduction of a clutter component;
a fourth process of calculating a filter coefficient for reduction of the clutter component on a basis of the plurality of eigenvectors, and the reduction rate corresponding to each of the plurality of eigenvectors; and
a fifth process of generating blood flow image data by applying the filter coefficient to the time-series reflection wave data group.

14. The ultrasound diagnostic apparatus according to claim 1,
wherein the frequency analyzation includes calculating a phase difference component of the time direction represented by the eigenvector of each order and converting the phase difference component of the time direction into a frequency component of the time direction.

* * * * *